(12) United States Patent
Armstrong et al.

(10) Patent No.: US 9,005,269 B2
(45) Date of Patent: Apr. 14, 2015

(54) BIOABSORBABLE SELF-EXPANDING ENDOLUMENAL DEVICES

(75) Inventors: Joseph R. Armstrong, Flagstaff, AZ (US); Paul C. Begovac, Flagstaff, AZ (US); Robert L. Cleek, Flagstaff, AZ (US); Edward H. Cully, Flagstaff, AZ (US); Charles Flynn, Flagstaff, AZ (US); Byron K. Hayes, Flagstaff, AZ (US); Ryan V. Peterson, Flagstaff, AZ (US); Michael J. Vonesh, Flagstaff, AZ (US); Charles F. White, Camp Verde, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 610 days.

(21) Appl. No.: 12/181,197

(22) Filed: Jul. 28, 2008

(65) Prior Publication Data
US 2008/0281393 A1 Nov. 13, 2008

Related U.S. Application Data

(63) Continuation of application No. 10/910,502, filed on Aug. 2, 2004, now abandoned.

(51) Int. Cl.
*A61F 2/82* (2013.01)
*A61F 2/01* (2006.01)
(Continued)

(52) U.S. Cl.
CPC ............ *A61F 2/01* (2013.01); *A61B 17/12022* (2013.01); *A61B 17/12118* (2013.01);
(Continued)

(58) Field of Classification Search
CPC ..................................... A61F 2/01; A61F 2/82
USPC ........... 623/1.17, 1.14, 1.15, 1.16, 1.36, 1.38; 600/198, 200
See application file for complete search history.

(56) References Cited

U.S. PATENT DOCUMENTS

| 4,187,390 A * | 2/1980 | Gore ...................... 174/102 R |
| 4,429,080 A | 1/1984 | Casey et al. |

(Continued)

FOREIGN PATENT DOCUMENTS

| WO | WO 01/03607 | 1/2001 |
| WO | WO02/096272 | 12/2002 |
| WO | WO 2004/045474 | 6/2004 |

OTHER PUBLICATIONS

Middleton JC, Tipton, AJ Synthetic biodegradable polymers as orthopedic devices. Biomaterials 2000; pp. 2335-2346.
(Continued)

*Primary Examiner* — Christopher D Prone
(74) *Attorney, Agent, or Firm* — Amy L. Miller

(57) ABSTRACT

Bioabsorbable self-expanding medical devices formed of an integral framework with a multiplicity of fenestrations are provided. The framework is continuous, non-filamentous, non-braided, and non-interlaced. The devices includes a non-blended hydrolysable co-polymeric material comprising an amorphous component with a glass transition temperature that is below ambient body temperature and a crystallizable component that possesses a crystalline melting point in excess of ambient body temperature. The devices radially expand from a compressed first diameter to an uncompressed second diameter equal to or greater than 1.5 times the first diameter within two minutes in an aqueous medium at 37° C. following release of a compressive force placed on the devices. Additionally, the medical device does not change axial length significantly as the radial dimensions of the devices are changed. Further, the medical devices may be constructed of different bioabsorbable polymers, polymer ratios, and/or different geometries and portions may bioabsorb at different rates.

22 Claims, 18 Drawing Sheets

(51) Int. Cl.
  *A61B 17/12* (2006.01)
  *A61F 2/91* (2013.01)
  *A61F 2/915* (2013.01)
  *A61L 31/06* (2006.01)
  *A61L 31/14* (2006.01)
  A61F 2/30 (2006.01)

(52) U.S. Cl.
  CPC ..... *A61B17/1214* (2013.01); *A61B 2017/1205* (2013.01); *A61F 2/91* (2013.01); *A61F 2/915* (2013.01); *A61F 2002/018* (2013.01); *A61F 2002/30062* (2013.01); *A61F 2002/91508* (2013.01); *A61F 2002/91525* (2013.01); *A61F 2002/91533* (2013.01); *A61F 2002/9155* (2013.01); *A61F 2210/0004* (2013.01); *A61F 2250/003* (2013.01); *A61L 31/06* (2013.01); *A61L 31/148* (2013.01); *A61F 2002/016* (2013.01); *A61F 2230/005* (2013.01); *A61F 2230/0069* (2013.01); *A61F 2230/008* (2013.01); *A61F 2210/0076* (2013.01); *A61F 2220/0016* (2013.01); *A61F 2230/0054* (2013.01)

(56) References Cited

U.S. PATENT DOCUMENTS

| | | |
|---|---|---|
| 4,950,258 A | 8/1990 | Kawai et al. |
| 5,147,385 A | 9/1992 | Beck et al. |
| 5,240,553 A | 8/1993 | Jones |
| 5,486,546 A | 1/1996 | Mathiesen et al. |
| 5,500,013 A | 3/1996 | Buscemi et al. |
| 5,603,720 A | 2/1997 | Kieturakis |
| 5,670,161 A | 9/1997 | Healy et al. |
| 5,873,904 A | 2/1999 | Ragheb et al. |
| 5,935,506 A | 8/1999 | Schmitz et al. |
| 6,001,123 A | 12/1999 | Lau |
| 6,004,347 A * | 12/1999 | McNamara et al. ....... 623/23.64 |
| 6,045,568 A | 4/2000 | Igaki et al. |
| 6,171,338 B1 * | 1/2001 | Talja et al. .................. 623/1.22 |
| 6,179,859 B1 * | 1/2001 | Bates et al. .................. 606/200 |
| 6,200,335 B1 | 3/2001 | Igaki |
| 6,228,111 B1 | 5/2001 | Tormala et al. |
| 6,245,103 B1 | 6/2001 | Stinson |
| 6,254,632 B1 | 7/2001 | Wu et al. |
| 6,258,121 B1 | 7/2001 | Yang et al. |
| 6,281,262 B1 | 8/2001 | Shikinami |
| 6,287,332 B1 | 9/2001 | Bolz et al. |
| 6,344,055 B1 | 2/2002 | Shukov |
| 6,368,346 B1 | 4/2002 | Jadhav |
| 6,371,979 B1 | 4/2002 | Beyar et al. |
| 6,423,092 B2 | 7/2002 | Datta et al. |
| 6,537,312 B2 | 3/2003 | Datta et al. |
| 6,563,080 B2 | 5/2003 | Shapovalov et al. |
| 6,613,072 B2 | 9/2003 | Lau et al. |
| 6,632,242 B2 | 10/2003 | Igaki |
| 2001/0047202 A1 * | 11/2001 | Slaikeu et al. ............... 623/1.46 |
| 2003/0040754 A1 | 2/2003 | Mitchell et al. |
| 2003/0040772 A1 * | 2/2003 | Hyodoh et al. ............... 606/200 |
| 2003/0069629 A1 * | 4/2003 | Jadhav et al. ................ 623/1.15 |
| 2003/0069929 A1 | 4/2003 | Millikan et al. |
| 2003/0074049 A1 | 4/2003 | Hoganson et al. |
| 2003/0083646 A1 * | 5/2003 | Sirhan et al. ................ 604/891.1 |
| 2003/0153971 A1 | 8/2003 | Chandrasekaran |
| 2003/0153972 A1 | 8/2003 | Helmus |
| 2005/0283226 A1 * | 12/2005 | Haverkost .................... 623/1.15 |

OTHER PUBLICATIONS

Benicewicz BC, Hopper, PK Polymers for Absorbable Surgical Sutures—Part I. Journal of Bioactive and Compatible Polymers Oct. 1990; 5:453-472.

* cited by examiner

BIOABSORBABLE SELF-EXPANDING ENDOLUMENAL DEVICES

CROSS-REFERENCE TO RELATED APPLICATIONS

This application is a continuation of application Ser. No. 10/910,502, filed Aug. 2, 2004 now abandoned.

FIELD OF THE INVENTION

The present invention is directed to implantable medical devices. In particular, the invention is directed to self-expanding bioabsorbable endolumenal devices.

BACKGROUND OF THE INVENTION

A variety of implantable medical devices have been developed to treat diseased, injured, or deformed body conduits. In cases where malfunctioning body conduits have reduced inner diameters, there is usually reduced flow of vital fluid or gas through the conduits. In extreme cases, the malfunctioning conduits are occluded. Implantable medical devices used to open and/or expand, or to otherwise treat obstructed or constricted body conduits often reside in the conduits for a period of time following deployment of the devices. The devices serve primarily as mechanical supports inside the malfunctioning conduits to help maintain the conduits in more open, or patent, conditions.

These types of implantable medical devices are usually threaded through a healthy body conduit with a catheter, or other delivery mechanism, to a diseased area of the body conduit where the devices are employed. Many of these devices are frameworks made of a deformable metal suitable for implantation, such as stainless steel, cobalt-chromium, and other precious metals and/or alloys thereof. The devices are often employed with the aid of a balloon placed within the device framework that expands the framework until it presses against and engages the inside, or lumenal, wall of the body conduit. Other devices have combinations of configurations and material compositions that enable the devices to "self-expand" from a compacted shape to an expanded conformation without the aid of an inflatable balloon or other mechanical expansion means. Some devices are self-expanding under the influence of thermal or stored elastic energy alone. These devices are typically made with a shape-memory metal alloy commonly referred to as a super-elastic nickel-titanium composition (Nitinol). Shape-memory devices are intended to reduce or eliminate the need for an inflatable balloon.

Despite these and other advances in such implantable metal devices, the devices remain in the body conduit after palliation, treatment, or cure has been effected. While leaving the device in place may be benign in some situations, in other situations it would be preferred if the device did not remain in the body conduit. Of particular concern in leaving a metallic implant in a patient is the negative impact a subsequent procedure may have on the patient as a result of the implanted device. For example, the strong magnetic field produced by a magnetic resonance imaging (MRI) machine can adversely interact with the metallic implant. Also, the presence of a chronically implanted device can cause abrasions or erosions to tissue in which the device is implanted. Additionally, a subsequent endoluminal procedure can also result in an adverse encounter, or interaction, with a previously implanted device.

One approach to removing an implantable medical device from a body conduit has been to construct the device from certain polymeric materials that are either absorbed or degraded by physiological processes of the implant recipient. Bioabsorbable implants are constructed of polymeric materials designed to be benignly absorbed by the body over time. Materials capable of bioabsorption are also referred to as "absorbable," "bioresorbable," "resorbable," "degradable," and "biodegradable." All these terms are all considered herein as synonymous with the term bioabsorbable with regard to the present invention.

The most common, bioabsorbable polymeric materials are removed from an implant recipient by hydrolysis of the polymeric material into metabolites, or break down products, that are substantially non-toxic to the implant recipient. The absorption of bioabsorbable polymeric materials typically begins by exposing the bio-absorbable material to aqueous fluids and/or certain enzymes under normal physiological conditions. The bioabsorption process usually continues until the device is entirely gone from the body conduit, or other implant site.

The particular polymers used to make an implantable medical device determine many of the properties of the device. Of particular significance are the biocompatibility of the bioabsorbable polymer and breakdown products thereof, bioabsorption rate, mechanical compatibility and compliance with tissue in which the device is implanted, rate of expansion, if any, mechanical strength of the device, and geometrical design.

An example of a mechanically expandable degradable stent that is tissue compliant, but of poor strength is disclosed by Beck et al. in U.S. Pat. No. 5,147,385. The stent of Beck et al. is made of poly($\epsilon$-caprolactone) polymer. According to Beck et al., the poly($\epsilon$-caprolactone) polymer melts in a temperature range between forty-five (45) and seventy-five (75) degrees centigrade. This is said to confer an ability to melt and mold the stent to the body lumen as the stent is being deployed in the lumen with the assistance of a heated balloon catheter. Unfortunately, when the polymeric material used to make the stent is placed inside a body conduit and raised above its melt temperature to undergo a re-modeling process, any inconsistency or inadequacy in thermal transfer from the heated balloon to the device as it is deployed can cause irregular and potentially unpredictable device deformations. Consequently, implantable medical devices intended for use as degradable stents or other temporary scaffoldings for a body conduit made of poly($\epsilon$-caprolactone), or similar homopolymers that require a thermal softening or melting transition above normal human body temperature in order to expand, are likely to lack sufficient reliable mechanical strength to be practical devices.

Another problematic expandable biodegradable stent is disclosed by Healy et al. in U.S. Pat. No. 5,670,161. The Healy et al. stent is made of a copolymer of l-lactide and $\epsilon$-caprolactone that needs to be heated near or above its glass transition temperature ($T_g$) to be expanded. The stent's in vivo mechanical strength is dependent on the properties imparted by the glassy state existing below the copolymer's Tg. The stent is described as expandable using a "thermally-assisted mechanical expansion process at a temperature between about 38 degrees centigrade and 55 degrees centigrade." Hence, the Healy et al. stent does not expand at normal human body temperature of 37 degrees centigrade and is also described as risking a "potentially hazardous" fracture if expansion is attempted in the brittle and glassy state found below the Tg of the stent.

As with Beck et al., the Healy et al. stent must be reliably heated above normal human body temperature and undergo a thermal transition before it can be safely remodeled by plastic deformation, expand, and become deployed. Healy et al. indicate a stent can be fashioned from a copolymer of l-lactide and ε-caprolactone that achieves a balance between sufficient mechanical strength to support a body lumen and the ability to remodel and expand the stent just above normal human body temperature. While this may be the case, an expandable endolumenal device made of a copolymer of l-lactide and ε-caprolactone requiring a thermal transition above normal human body temperature will always require application of heat to the device in excess of normal body temperature while it is inside the body conduit.

A biodegradable lactic acid-based polymeric material exhibiting "shape memory" properties for use in constructing implantable medical devices is disclosed by Shikinami in U.S. Pat. No. 6,281,262. Among the various medical devices that can be made with the Shikinami material, expandable supports for body conduits are disclosed. The supports are initially made in a cylindrical shape and subsequently collapsed into a secondary shape at a raised temperature. Upon cooling below the glass transition temperature ($T_g$) of the polymer, the support remains in the secondary collapsed state. When the support is reheated to a temperature ($T_f$) higher than the glass transition temperature ($T_g$), but below the crystallization temperature ($T_c$) of the polymeric material, the support reverts to its initial shape.

The primary polymer is poly-d,l-lactic acid. The ratios of the lactic acid isomers used in the polymer can be varied to achieve different thermal transition properties of the final polymeric material. The primary polymer can be mixed, or blended, with other biodegradable or bioabsorbable polymers, such as crystalline poly-l-lactic acid, poly-d-lactic acid, polyglycolic acid, amorphous polydioxanone, polycaprolactone, or polytrimethylene carbonate. Shikinami points out that regardless of the particular polymeric material chosen for use in his invention, the "shape-recovering treatment" should be performed at a temperature above normal human body temperature between 45 degrees and 100 degrees centigrade.

Devices requiring in situ application of heat above normal human body temperature are problematical at best. In addition to the possibility of causing patient discomfort in the form of pain with such a procedure, local trauma to same tissue intended to be medically treated with the device is also a possibility. Furthermore, it is unknown whether such trauma to "lumenal tissue" will stimulate undesirable tissue processes to begin at the implant site, such as a hyperplasia.

Stinson in U.S. Pat. No. 6,245,103 discloses a self-expanding stent constructed from bioabsorbable filaments that is self-expanding without the application of heat. The stent is said to have radial strength similar to metal stents by virtue of the braided construction of the stent and the chemical structure of certain filaments. The tubular self-expanding stent of Stinson is made by helically winding and interweaving resilient filaments of a bioabsorbable material into a particular braided configuration. Radial strength is imparted to the braided stent through use of two sets of interwoven filaments acting upon one another to "create an outwardly directed radial force sufficient to implant the stent in a body vessel upon deployment from a delivery device."

As the stent changes shape from a compacted to an expanded configuration, the radius of the stent is increased and the axial length is decreased. According to Stinson, the shortening of the device can be predicted and compensated for. While this may be the case, shortening of the stent may not be acceptable in some applications, such as cardiovascular applications.

A similar bioresorbable self-expanding stent made of braided filaments is disclosed by Jadhav in U.S. Pat. No. 6,368,346. The principle teaching of Jadhav is the use of blends of bioresorbable polymers instead of co-polymers to make the filaments. Blended polymers are preferred by Jadhav because the chemical composition of the filament material is said to be more easily adjusted with blending than by synthesizing a new batch of co-polymer material. Blending is also said to reduce batch to batch variation common with synthesized co-polymers. As with Stinson, supra, the braided filaments form a tubular structure that shortens in length upon radial expansion of the compressed stent.

Jadhav also discloses an embodiment of a radially self-expanding extruded tubular stent made with blended bioresorbable polymers. The stent has walls that may be populated with openings. As with the braided stent, Jadhav's extruded stent is also "axially retractable" and shortens in length as it increases in diameter and radially expands. Excessive shortening (e.g., greater than about ten percent (10%) during deployment can result in deployment inaccuracy and cause intragenic trauma to wall tissue of the body conduit.

Igaki discloses a stent in U.S. Pat. No. 6,200,335 that is intended to be more compliant with tissue in which the stent is implanted. In this pursuit, the walls of the stent are gradually decreased in thickness toward each end of the stent. Additional flexibility can be imparted to the stent by introducing holes in the tapered wall material. The combination results in a stent structure with a Young's modulus equal to or slightly larger than $3 \times 10^7$ pascal, which Igaki describes as approximately representative of a blood vessel. Though primarily directed to a metallic stent, Igaki indicates his tubular stent can be made by extruding or injection molding a polymer material that has "biological absorptivity." None of Igaki's stents are said to be compressible or expandable. Rather, the stents are referred to simply as inserts. The advantages of an endoluminal device that is both compressible for transport through a body conduit and expandable for delivery of the device to an implantation site are well known and appreciated in the surgical arts.

Virtually all of the above-summarized bioabsorbable stents rely on the readily available α-hydroxy ester polymers and copolymers derived from glycolide and lactide. While these monomeric components provide a predictable resorption rate by virtue of their hydrolyzable bonds, the monomers contribute only limited amounts of freely rotating aliphatic component into the polymer chain. As a result, polyglycolic acid (PGA) possesses a relatively high glass transition temperature ($T_g$) of approximately 36° C. (Benicewicz B C, Hopper P K., "Polymer for Absorbable Surgical Sutures—Part I," *Journal of Bioactive and Compatible Polymers*, 5:453-472 (1990)) while polylactic acid (PLA) delivers a $T_g$ of approximately 52° C. (Middleton J C, Tipton A J., "Synthetic Biodegradable Polymers as Orthopedic Devices," *Biomaterials* 21:2335-2346 (2000)). Additionally, both polyglycolide (PGA) and single isomeric forms of polylactide (d-PLA or l-PLA) carry the potential for crystallization, imparting both dimensional stability and increasing polymer rigidity.

To impart some improved flexibility to the polymeric chain, many of the above-summarized references utilize either blending or co-polymerization of the α-hydroxy ester with polycaprolactone, a polyester which utilizes a monomer possessing a larger aliphatic component of five successive methylene groups. This increased aliphatic component provides polycaprolactone with greater amorphous state flexibility and a significantly lower Tg than the α-hydroxy esters. While the rotational features of this relatively extended aliphatic chain component impart improved chain mobility and a resulting $T_g$ of approximately minus sixty degrees centigrade (−60° C.) (Middleton J C, Tipton A J., "Synthetic Biodegradable Polymers as Orthopedic Devices," *Biomaterials* 21:2335-2346 (2000)), this rotational benefit is somewhat counteracted by polycaprolactone's tendency to crystallize with the accompanying rigidity.

It is these combined structural properties of the α-hydroxyester and caprolactone-based polymers that impart the specific thermal and flexural characteristics to these bioabsorbable stent constructions that require application of heat above normal body temperature and/or extrinsically applied force to deploy the device. It is noteworthy that polycaprolaction homopolymer has particularly longevity in vivo.

In addition to the inherent mechanical weakness conferred on the above-summarized devices by the polymers and processes from which they are formed and deployed, as discussed above, there are dangers inherent in applying heat to implantable devices, particularly endoluminal devices, at the implantation site. It would be desirable, therefore, if the polymeric material of an implantable medical device could reliably change shape, or conformation, without the need for the material to undergo a thermal transition, and especially without need for application of heat to the device at the implantation site. A non-elongating, self-expanding, implantable medical device made of biocompatible materials allowing the device to assume an expanded configuration when deployed at or near body temperature has numerous clinical benefits.

There is a need, therefore, for a non-elongating self-expanding support for a body conduit made of materials configured to allow the support to be reliably deployed inside or outside a body conduit at, or below, normal human body temperature. There is a further need for a support for a body conduit that is bioabsorbed into the body within approximately one year of implantation to assure complete removal of the support from the implantation site and, if needed, provide the opportunity in a subsequent procedure to implant another device.

None of the above-summarized stents meet the needs of an implantable medical device for use in a body conduit that is constructed from a non-blended hydrolyzable polymeric material as an integral flexible fenestrated framework that does not substantially change axial length with radial compression and expansion of the stent and is self-expanding at, or below, normal human body temperature without the polymeric material undergoing a thermal transition. Nor do the devices provide for variable bioabsorption rates in different parts, segments, or portions of the devices.

SUMMARY OF THE INVENTION

The present invention is directed to bioabsorbable medical devices for use inside or outside body conduits that self-expand at, or below, normal human body temperature without the polymeric material from which the invention is made undergoing a thermal transition. The devices are implanted in diseased, traumatized, or deformed tissue having lumenal space that is pathologically decreased in size. The devices are usually transported to an implantation site though a healthy portion of a body conduit with a catheter, or other delivery means, in a compacted configuration. The devices are usually restrained in the compacted configuration within a portion of the delivery catheter or placed on the delivery catheter and constrained within an overlying cover, or sheath. When contained within a catheter, the devices can simply be pushed out of an open distal end of the catheter with appropriate means. With delivery systems using constraining sheaths, the sheath is retractable from the devices with an actuation mechanism incorporated into the catheter, or other mechanism such as the "Deployment System For An Expandable Medical Device" disclosed in U.S. patent application Ser. No. (unassigned), filed Jul. 16, 2004 which is a continuation-in-part of copending application Ser. No. 10/637,986, filed Aug. 8, 2003, which is a continuation-in-part of co-pending application Ser. No. 10/346,598, filed Jan. 17, 2003.

As the radial constraint is removed from devices of the present invention, the devices are freed to increase in diameter without requiring an extrinsically applied force and/or undergoing a thermal transition. The freed devices continue to self-expand, contact wall tissue delimiting the lumenal space, and press radially outward against the tissue wall until the devices are implanted, embedded, or otherwise immobilized in the wall tissue. Once implanted, the devices provide mechanical support or other medical benefit to the tissue wall of the body conduit. The device continues to operate until the bioabsorbable material of the device is absorbed to the point where the device is diminished and eventually completely bioabsorbed.

In some embodiments, a device of the present invention is delivered to the implantation site installed over an inflatable balloon. If the diameter of the body conduit needs to be increased, or dilated, in combination with implantation of the device, the balloon can be inflated as the device is freed and pressed against the tissue wall along with the device. The inflatable balloon can also be used to fully expand a partially expanded self-expanding device.

Devices of the present invention are preferentially made of non-blended hydrolyzable co-polymeric materials. These polymers have a combination of an α-hydroxy ester and a soft non-crystallizing segment that imparts added resilience to the device. Possession of an α-hydroxy ester component bestows the device with a predictable hydrolytic rate that accompanies ester functionality. As a result, the hydrolytically controlled degradation is minimally affected by enzymatic activity and is thereby consistent across implant hosts.

The polymeric materials used in the present invention are not blended. Rather, the polymeric components are covalently bonded to produce a non-blended block co-polymer. Blending of two or more polymers carries with it the risk of polymer migration, potentially leading to concentration gradients and possible separation of the constituent polymers into distinct phases, all of which risk affecting the physical and/or mechanical properties of a bioabsorbable device. Such migration can occur at any time after fabrication depending both on the actual composition and the environment to which the implant is exposed. Particular concern for migration arises at elevated temperature and under gas sterilization conditions.

Devices of the present invention made with these polymeric materials do not require a thermal transition to radially expand from a compressed first diameter to an uncompressed second diameter equal to or greater than one and a half (1.5) times the first diameter within two (2) minutes in an aqueous medium at thirty-seven (37) degrees centigrade following release of a compressive force placed on the devices. In addition, the devices do not require an extrinsically applied force to change from a compressed configuration to an uncompressed, or expanded, form. Devices of the present invention having these properties are referred to herein as "self-expanding."

The non-blended hydrolyzable co-polymeric materials used to construct devices of the present invention (10) are in the form of an integral framework (12) populated with a multiplicity of fenestrations (14), or holes. An integral framework of the present invention is not made of filamentous or wire-like materials. Accordingly, the integral framework of the present invention is not woven or braided with bio-absorbable polymeric material, or an otherwise interlaced construction. A woven or braided framework requires the filamentous components of the weave or braid to slide past one another, generally resulting in stent elongation when exposed to compressive forces. The integral framework of the present invention does not elongate as the device is radially expanded.

Inter alia, the present invention can be deployed in vital small diameter body conduits, like cardiovascular structures. These applications often require precise placement of the devices in the body conduit. Devices that shorten in length as they radially expand do not readily lend themselves to the precise placement required in these applications. Properly imaged devices of the present invention can be precisely placed in a body conduit because the integral framework of the devices does not shorten in length during radial expansion and implantation. Devices of the present invention that do not change axial length significantly (i.e., greater than about ten percent (10%) as the radial dimensions of the devices are changed are referred to herein as "non-elongating."

Though sufficiently strong to resist radially compressive forces from tissue in which devices of the present invention are implanted, the devices have a Young's modulus equal to or less than the tissue in which the devices are implanted. Accordingly, tubular devices of the present invention have integral non-elongating frameworks with a Young's tensile modulus of approximately than $2.1 \times 10^6$ Pascals when evaluated longitudinally in an open, uncompressed, and unrestrained (i.e. fully deployed) configuration. Devices of the present invention are very compliant with implanted tissue as a consequence. A multiplicity of fenestrations is provided in the integral framework to further enhance tissue compliance of the devices and permit tissue ingrowth. Tissue ingrowth can further anchor the devices.

An object of the present invention is to provide a self-expanding, non-elongating, bio-absorbable support for a body conduit that is made of non-blended hydrolyzable polymeric compounds of known composition, mechanical properties, and bio-absorption rates that allow the device to be reliably deployed with conventional delivery means under aqueous conditions at, or below, normal human body temperature without undergoing a thermal transition. The device can be constructed so it is completely absorbed by the implant recipient within one (1) year following implantation.

Accordingly, one embodiment of the present invention is an implantable medical device comprising an integral framework delimiting a multiplicity of fenestrations, said framework comprising a non-blended hydrolyzable polymeric material, and wherein said framework is substantially tubular in shape and radially expands from a compressed first diameter to an uncompressed second diameter equal to or greater than 1.5 times said first diameter within two minutes following application and release of a compressive force while immersed in an aqueous medium at 37 degrees centigrade without requisite for an extrinsically applied force and without requisite for a thermal transition.

Since the present invention is intended to permit fluid, including gas, to pass through the device once implanted in a body conduit, the invention is usually configured in a generally tubular geometry. In some applications, the present invention can serve as a filtration device instead of, or addition to, a support for a body conduit. Devices of the present invention having filtration properties are generally conical, or tapered, in shape. In these filtration devices, fluid flows through the fenestrations of the framework. As with the tubular configuration of the present invention, these other configurations of the invention are also self-expanding.

In these embodiments, the present invention comprises an integral framework delimiting a multiplicity of fenestrations, said framework comprising a non-blended hydrolyzable polymeric material, and wherein said framework has an axial length and a shape that is circular in cross-section and radially expands from a compressed first diameter to an uncompressed second diameter equal to or greater than 1.5 times said first diameter within two minutes following application and release of a compressive force while immersed in an aqueous medium at 37 degrees centigrade without requisite for an extrinsically applied force and without requisite for a thermal transition. Preferred embodiments have a circular cross-section that varies in diameter along the axial length of the device.

These and other embodiments of the present invention can be made of bioabsorbable materials having parts, segments, or portions with a geometry that is different from another part, segment, or portion of the device. As a consequence, the bioabsorbable material has mass in one portion of the device different from another portion. These differences can directly effect the mechanical properties and function of the invention.

In yet other embodiments, different parts, segments, or portions of the present invention are constructed of bioabsorbable polymers having different chemical compositions. The bioabsorption rate of each particular polymer composition will vary depending on the composition. Hence, the rate of bioabsorption in one part, segment, or portion of the device is different than the bioabsorption rate in another part, segment, or portion of the device.

Embodiments of the present invention can combine these features in a single construction having framework members of different geometries and chemical compositions. A device of the present invention constructed of different bioabsorbable polymers, polymer ratios, and/or different geometries will have portions that are bioabsorbed at different rates. Devices having any or all of these variable bioabsorption properties are referred to herein as having a "programmed rate of bioabsorption."

A preferred embodiment of a filtration device of the present invention has a series of frame elements, or struts, forming a substantially conical configuration with openings between the struts for fluid flow therethrough. The struts are tapered in width along their length and narrow toward the center of the conical structure. The mechanical performance of a particular portion of the invention is dependent on the geometry of the portion. As a consequence, the narrower portions of the tapered struts near the center of the device are removed from the body conduit at a faster rate than the wider portions of the struts at the periphery of the filtration device.

In another embodiment, the filtration device has a series of frame elements, or struts, forming a substantially conical configuration with openings between the struts for fluid flow therethrough. The frame elements are made of bioabsorbable polymeric materials that have different chemical compositions in different locations of the frame elements.

In yet another embodiment, both types of frame elements are used in combination to form a filtration device for a body conduit of the present invention.

Non-absorbable, metallic, strut members can also be combined with the bioabsorbable configurations and devices of the present invention.

DESCRIPTION OF THE INVENTION

Figure 1:
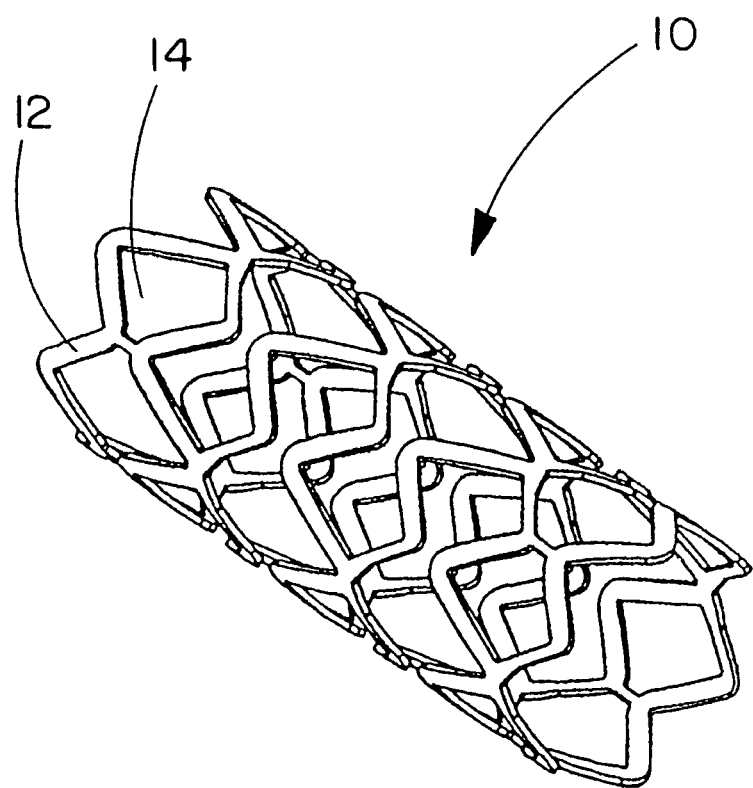
FIG. 1 illustrates an isometric view of a device of the present invention in a radially expanded configuration.

The present invention is directed to implantable bioabsorbable medical devices suitable for use inside or outside anatomical structures, such as body conduits. The invention is particularly suited for use as support members, filters, and/or drug delivery vehicles for the anatomical structures. The present invention provides both self-expandability and resistance to compression forces in vivo. The polymeric material used to construct the invention incorporates sufficient resilience to avert permanent deformation, or collapse, of the invention upon exposure to either circumferential or point loading in vivo. Resistance to permanent compressive distortion is maintained by the invention during construction, sterilization, storage, deployment, implantation, and the early stages of bioabsorption.

Previously disclosed devices fabricated from amorphous polymers are limited to service conditions that are below their Tg due to the tendency of the amorphous polymers to deform in response to applied stress at temperatures in excess of their Tg. For example, a construction formed of an amorphous polymer with a Tg of 30° C. should, within its elastic limit, retain significant strength under room temperature mechanical testing conditions to avoid deformation because the polymer exists in its relatively hard glassy state. Conversely, the same construction is expected to deform or even irreversibly collapse when compressed under mechanical load after the polymer has transitioned into the rubbery state present under aqueous conditions at 37° C.

To maintain effective radial and compressive strength within such an amorphous polymer system, the effective Tg of the polymer system must be above the expected service temperature of the device (37° C. in vivo). One of the drawbacks of an amorphous system operating below its Tg is a reduced level of chain mobility in the glassy state in which the polymeric system exists. This limited chain mobility carries the benefit of increased strength and resistance to deformation, but runs greater risk of plastic deformation under loads sufficient to generate dimensional distortion. Further, when such a system is effectively frozen into its glassy state, the system possesses increased potential to impart a negative bioresponse due to polymeric cohesion and related mechanical rigidity. Additionally, accommodation for the thermal transition at the time of loading and deployment is needed in order to provide self-expanding characteristics similar to those of the present invention.

The present invention utilizes a polymer system that possesses a Tg below the expected service temperature, but also possesses a semi-crystalline polymeric component that imparts polymeric cross-linkage through the presence of crystallinity that is maintained in vivo, which in turn imparts reliable dimensional stability to the otherwise flexible implant structure. Such a polymeric system has less compressive strength, but also has both an increased ability to deflect under load and a reduced chance of plastic deformation—all by virtue of an amorphous phase existing in the rubbery state above its Tg.

Based on these and other physiochemical properties of polymer systems, the present invention utilizes an non-blended, block co-polymeric material that possesses both crystalline features and a co-polymeric Tg that is below the expected service temperature of 37° C. under aqueous conditions. Such a construction assures that, at the time of deployment under ambient physiological conditions, the device retains its dimensional stability, but remains flexible and tissue compliant by virtue of the rubbery state provided by service conditions above the system's Tg.

Since the soft flexible component of the co-polymeric material can be deformed upon loading at temperatures in excess of the Tg, dimensional stability under such conditions is functionally imparted at the time of crystallization or annealing of the invention. Such annealing can be imparted through the application of heat in excess of the Todt or with solvents able to penetrate the polymer interstices and functionally depress the polymer's Todt to ambient temperatures, or below.

For virtually any polymer system, the temperature of the glass transition can be experimentally determined through Differential Scanning Calorimetry (DSC) methods. For a copolymer system that is both amorphous and homogenously mixed, it is possible to calculate the Tg using the Fox equation, provided the Tg for the respective homopolymers and the weight fraction of each copolymeric component are known.

Fox Equation:

$$1/Tg = W_a/T_{ga} + W_b/T_{gb}$$

$T_{ga}$ and $T_{gb}$=the glass transition temperatures of polymers "a" and "b"

$W_a$ and $W_b$=the weight fraction of polymers "a" and "b"

Thus, the Fox equation provides ready utility in designing a copolymer for use in particular thermal service conditions known for a specific application. However, in crystallizable polymer systems where one of the components can effectively be removed from the amorphous phase, deviations from the Fox equation can be observed as the extent of crystallization progresses and the concentration of amorphous components are affected. Consequently, significant deviations from the value predicted by the Fox equation would be indicative of reduction of the respective constituent from the amorphous phase (i.e. entry into crystalline phase).

The glassy-rubber thermal transition present in the unstable mixed amorphous condition preceding crystallization of a crystallizable copolymeric segment is called the order-disorder transition ($T_{odt}$). This unstable transition also adheres to the Fox equation, allowing confirmation of the copolymeric ratios prior to segment crystallization. Additionally, the Fox equation can be utilized with the experimental Tg observed after full crystallization to evaluate the copolymeric ratio remaining within the amorphous non-crystalline phase. Thus, the Fox equation can be utilized to assess both the $T_{odt}$ and Tg for most copolymer systems with reasonable separation of glass transition temperatures.

The implantable semi-crystalline bioabsorbable polymeric medical devices of the present invention have a Tg at, or below, normal human body temperature and are suitable for use in body conduits. As a result of appropriate polymer selection and design, the invention radially self-expands within two minutes following application and release of a compressive force while immersed in an aqueous medium at 37 degrees centigrade from a compressed first diameter to an uncompressed second diameter equal to or greater than 1.5 times the first diameter without requisite for an extrinsically applied force and/or without requisite for a thermal transition.

This is accomplished by including both a rigid crystallizable alpha-hydroxy ester component and a flexible non-crystallizing component with increased aliphatic content within the polymer chain of the material used to construct the invention.

In the preferred embodiment (FIG. 1), a tri-block co-polymer of poly(glycolide) and poly(trimethylenecarbonate) having a weight to weight (w/w) ratio of poly(glycolide) to poly(trimethylenecarbonate) of 67% PGA:33% TMC is used to construct the invention. The geometry of the invention can be adapted to address a variety of medical applications. Since the TMC homopolymer possess a Tg of approximately minus seventeen degrees centigrade (−17° C.) (Albertsson A, Sjöing M., "Homopolymerization of 1,3 Dioxan-2-one to High Molecular weight Poly(trimethylene carbonate)," *J. Pure Appl. Chem. A*29(1):43-54 (1992)) the maximum possible Tg for this copolymer mixture as represented by the Todt and calculated by the Fox equation is approximately 17° C. The crystalline portions of the PGA copolymeric segment impart dimensional stability to the implant structure. Dimensional stability of the segment is reduced or lost by hydrolysis of ester bonds in the polymer resulting in significant scission of the polymer chain. The completely amorphous TMC copolymeric segment imparts predictable flexibility to the polymer system through its three methylene aliphatic components and limited potential for crystallization. This TMC component is believed to provide more reliable flexibility than caprolactone since homopolymeric TMC has a crystalline melt point of 36° C. and will not crystallize at all when its molecular weight exceeds 12,000 (Zhu K J, Hendren R W, Jensen K, Pitt C G. "Synthesis, proproties, and Biodegradation of Poly(1,3-trimethylene carbonate)," *Macromolecules* 24:1736-1740 (1991)). When synthesized together as a block copolymer, the resulting fully crystallized PGA:TMC copolymer combines dimensional stability with the ability to flex under load and then recover at or below human body temperature. The copolymer is readily processed into devices of the present invention.

67% PGA:33% TMC has been found to be virtually entirely bioabsorbed in vivo by the end of 6 months (Katz A R, Mukherjee D P, Kaganov A L, Gordon S., "A new synthetic monofilament absorbable suture made from polytrimethylene carbonate," *Surgery, Gynecology & Obstetrics* 161(3): 213-222 (1985)).

The PGA:TMC copolymerization is achieved by a sequential addition ring opening polymerization of the cyclic trimethylene carbonate and glycolide dimer monomers. Synthesis of PGA:TMC can be conducted to produce copolymers in segmented and/or simple block form. Methods for PGA:TMC synthesis are described in U.S. Pat. Nos. 4,243,775 and 4,300,565 both to Rosensaft, et al and U.S. Pat. No. 4,429,080 to Casey, et al., each of which is incorporated herein by reference.

Other desirable copolymeric ratios and/or block structures may necessitate the use of different variations in polymerization conditions and/or methods. For example, a fifty percent (50%) PGA, fifty percent (50%) TMC ratio of co-polymers, as disclosed in U.S. Pat. Nos. 6,165,217 and 6,309,423, may be useful in Examples 4, 7, and 9 below. Both glycolide and trimethylene carbonate monomers are available from BI Chemicals, Petersburg, Va. USA. A 33% weight to weight ratio of TMC to PGA segmented triblock copolymer may be obtained from United States Surgical, a unit of Tyco Healthcare Group LP, Norwalk, Conn.

Alternatively, the present invention can be fabricated from combinations of other biocompatible bioabsorbable monomeric components combined together to form a copolymer that possesses both an amorphous component with a Tg that is below ambient body temperature and a crystallizable segment that possesses a melting point in excess of ambient body temperature. Such copolymers can be comprised from varying amounts of one or more of the following monomer examples: glycolide, d,l-lactide, l-lactide, d-lactide, p-dioxanone (1,4-dioxane-2-one), trimethylene carbonate (1,3-dioxane-2-one), ϵ-caprolactone, gamma.-butyrolactone, delta.-valerolactone, 1,4-dioxepan-2-one, and 1,5-dioxepan-2-one. Other polymeric constituents of a bioabsorbable copolymer may include polyethylene glycol, polypropylene glycol, N-vinyl pyrrolidone, amino acids, anhydrides, orthoesters, phosphazines, amides, urethanes, and phosphoesters. Alternative copolymers may possess combinations of block, segmented, random, alternating, or statistical polymeric construction characteristics, provided the resulting copolymer ultimately delivers both an amorphous component with a Tg that is below ambient body temperature and a crystallizable component that possesses a crystalline melting point in excess of ambient body temperature.

The preferred embodiment of the present invention is bioabsorbable and radially expandable from a compressed first diameter to an uncompressed second diameter equal to or greater than 1.5 times said first diameter within two minutes following application and release of a compressive force while immersed in an aqueous medium at 37 degrees centigrade (37° C.) without requisite for an extrinsically applied force and without requisite for a thermal transition by using a copolymer system that delivers both a rigid crystallizable alpha hydroxy ester component and a flexible non-crystallizing component possessing increased aliphatic content.

Figure 9:
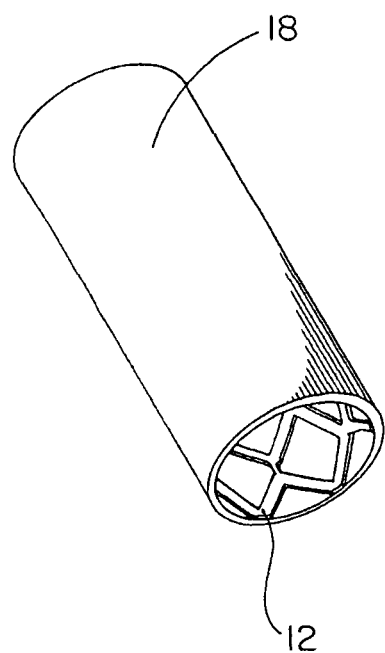
FIG. 9 illustrates an embodiment of the present invention having a covering over the integral framework.

As shown in FIG. 9, the present invention can be covered or enclosed with a polymeric material (18). The polymeric material can be non-bioabsorbable or bioabsorbable. Preferred non-bioabsorbable covering materials are fluoropolymeric materials, particularly polytetrafluoroethylene. The most preferred fluoropolymer is porous expanded polytetrafluoroethylene. Preferred bioabsorbable covering materials are films or webs of PGA:TMC, particularly those disclosed in U.S. Pat. Nos. 6,165,217 and 6,309,423.

While various bioactive therapeutic agents such as antithrombotic drugs including heparin, paclitaxol, dexamethasone and rapamycin are most commonly proposed to aid the performance of present invention, many others can also be used beneficially, either alone or in various combinations.

Therapeutic agents for a wide variety of applications can be used as additives with the coating for use with various embodiments of the invention. These agents include, but are not limited to, antithrombotic agents, anticoagulants, antiplatelet agents, thrombolytics, antiproliferatives, antiinflammatories, hyperplasia and restenosis inhibitors, smooth muscle cell inhibitors, antibiotics, antimicrobials, analgesics, anesthetics, growth factors, growth factor inhibitors, cell adhesion inhibitors, cell adhesion promoters and drugs that may enhance neointimal formation such as the growth of endothelial cells. Again, these therapeutic agents may be used alone or in various combinations, and may be in coatings that cover all surfaces of a device or only portions of a device.

Additives that are not bioactive and not elutable can be used, for example, various pigments, MRI-opaque additives or radiopaque additives (e.g., tantalum or gold). Pigments may be beneficially added to enhance direct visualization, for example, to provide a contrast against the blood of a surgical field. Pigments may also be used for printed indicia for various labeling or instructional purposes. Specialty pigments (e.g., luminescent) may be used for particular applications.

Figure 10:
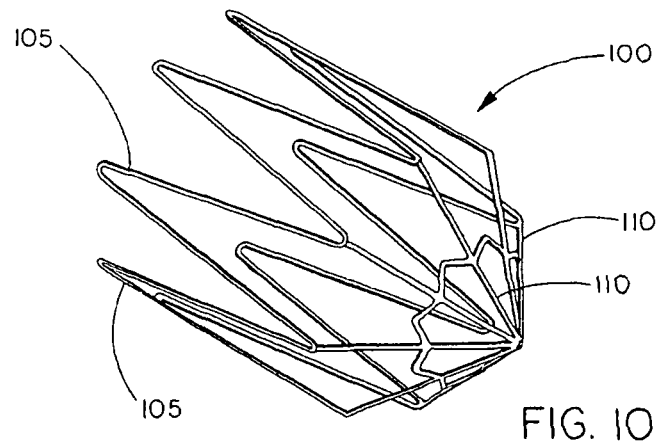
FIG. 10 is a perspective view of a bioabsorbable medical device configured as a blood filter.

The present invention can be configured in embodiments that serve as a filtration device. Referring to FIG. 10, filter device (100) is made of a bioabsorbable material that completely absorbs over time. Frame elements (105) and filter elements (110) are both made of bioabsorbable material. It may be especially useful if frame elements (105) are made of a different copolymer ratio than the filter elements (110). Altering copolymer ratios in areas of the same device allows the device to have a programmed rate of bioabsorption to ensure that the filter elements (110) dissolve before the frame elements.

Figure 11:
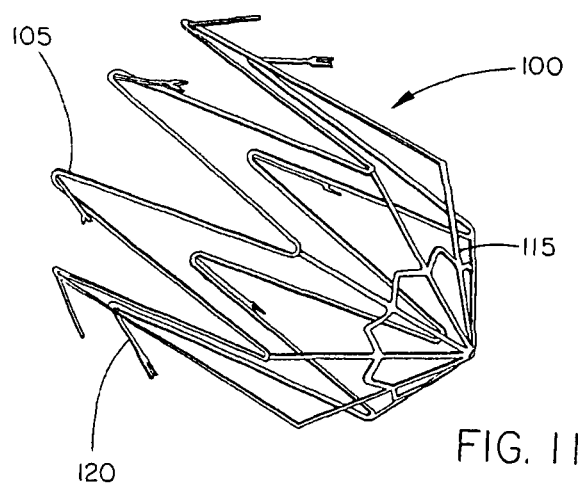
FIG. 11 depicts a partially bioabsorbable medical device configured as a blood filter.

FIG. 11 illustrates an alternate embodiment of a filter device (100) in which the frame elements (105) are metallic and bioabsorbable filter elements (115) are attached to them to form a composite device. This embodiment is shown with optional anchors (120). The metallic frame elements (105) in this configuration may be either plastically deformable or self-expanding, or a combination of both. As well, either the frame elements (105), filter elements (115) or both may incorporate radiopaque markers (not shown) to facilitate radiographic visualization. In this embodiment, filter elements (115) will dissolve at a predetermined time and frame elements will remain. Remaining frame elements will be in intimate contact with the host vessel wall and will not inhibit blood flow or the passage of subsequent interventional devices.

Figure 12:
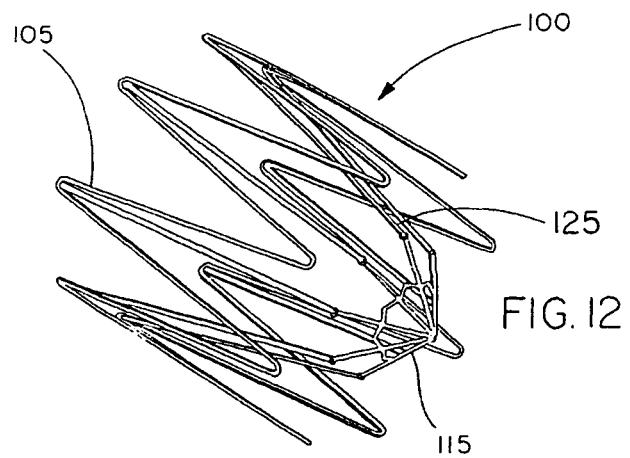
FIG. 12 depicts another version of a partially bioabsorbable medical device configured as a blood filter

Another embodiment of the partially absorbable filter device is illustrated in FIG. 12. In this embodiment, metallic frame elements (105) support and anchor the device in the vessel while bioabsorbable filter elements (115) are connected to filter suspension elements (125). The metallic frame elements (105) in this embodiment are preferably self-expanding. The geometry of filter elements (115) is configured to hold suspension elements (125) toward the center of a lumenal space of a body conduit and into the fluid flow therethrough, effectively causing suspension elements (125) to act as a portion of the filter region. Upon bioabsorption of the filter elements (115), the suspension elements (125) are freed and rebound of their own accord against the vessel wall and become transparent to fluid flow in the vessel. It should be apparent that the filter elements may also comprise the entire filter capacity of the device.

Figure 13:
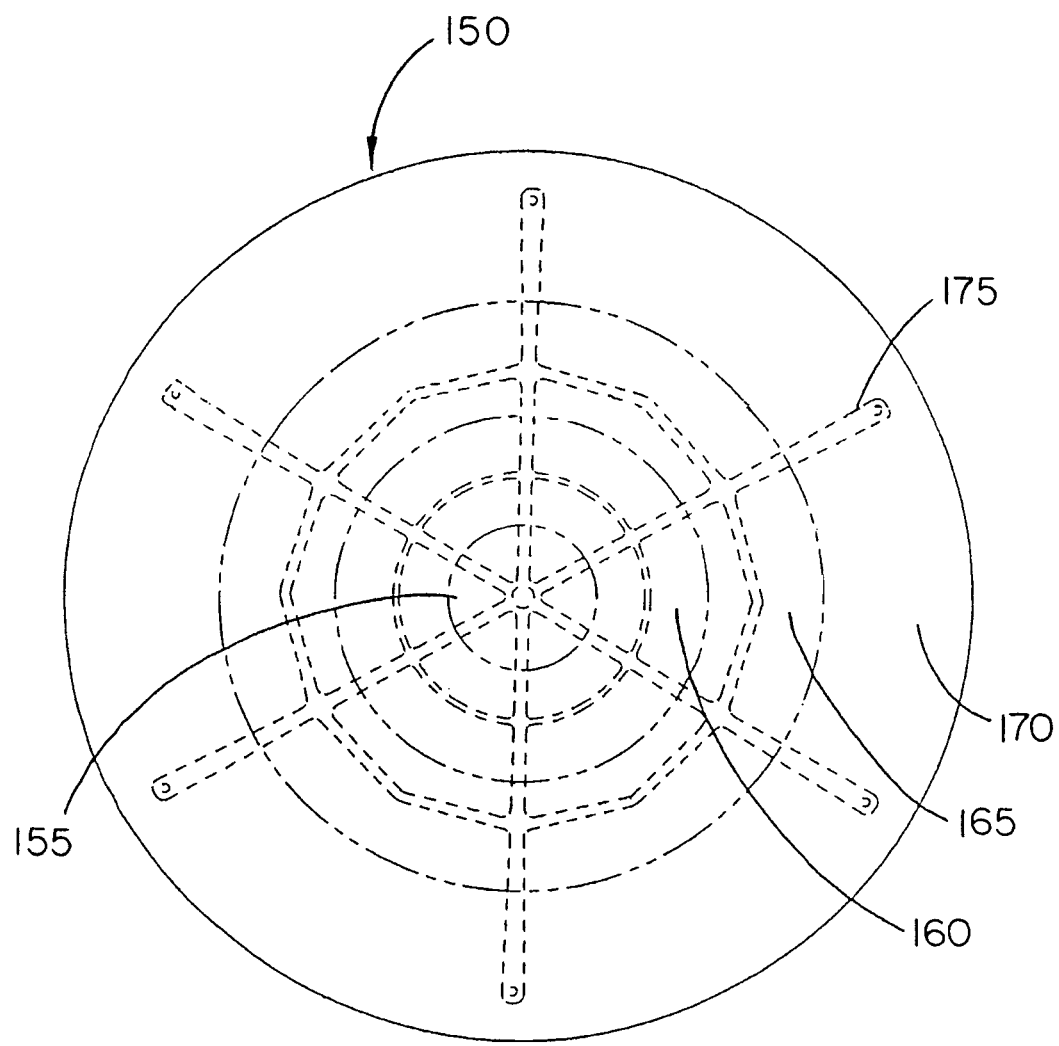
FIG. 13 depicts a planar sheet made from bioabsorbable material with concentric rings of varying copolymer ratios intended to have different absorption profiles.

The bioabsorbable precursor material (150) shown in FIG. 13 depicts a center zone (155) and three concentric rings (160), (165), and (170) of bioabsorable material. Each ring, or zone, contains a different copolymer ratio and thus will have different absorption rates, or profiles. In the case of a vena cava filter device for example, it would be preferred to have the bioabsorbable components dissolve beginning at the center of the lumenal space and gradually eroding outward toward the wall of the body conduit. In this case, copolymer ratios would be adjusted to allow center portion (155) to erode prior to concentric ring portion (160). Concentric ring portion (165) will erode before concentric ring portion (170) and so on. Although concentric rings are depicted, it should be apparent that other patterns incorporating different bioabsorption could be used. Hidden lines (175) depict one possible device configuration to be produced from this precursor bioabsorbable material. In other embodiments, the application may call for an erosion profile beginning at the periphery and progressing towards the center. In yet other applications, it may be suitable to program bioabsorption at alternating portions of the device, thus achieving a simulated checkerboard or mesh type configuration during the bioabsorbable decay cycle.

Figure 14:
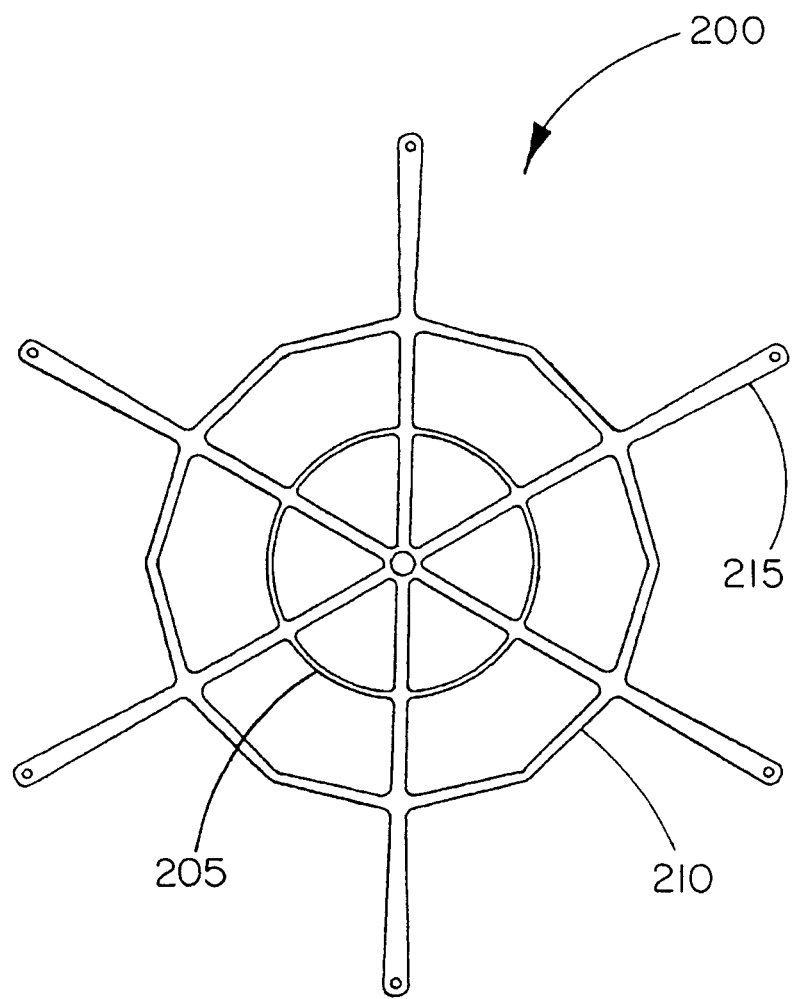
FIG. 14 depicts a planar sheet made from bioabsorbable material with varying geometric characteristics.

FIG. 14 shows a scheme in the programming of the mechanical function of the device. In this embodiment, the device (200) geometry dictates its mechanical characteristics.

Thin elements (205) will be under higher strain than the thicker elements (210). With this configuration, change in mechanical function is initiated at the center toward the vessel wall. Geometrical variations may be in both thickness and in width of the framework elements. Indeed, the variations may be three-dimensional. It should be noted that geometrical variations (tapered struts, etc) as shown here may be used in combination with altering copolymer ratios as described in FIG. 13.

Figure 15:
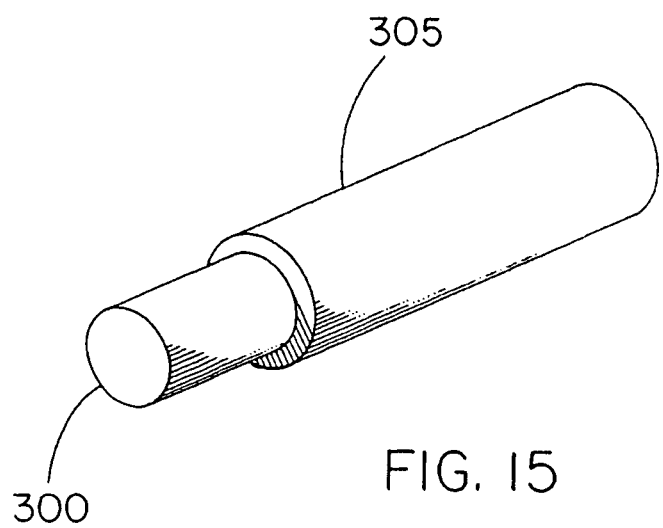
FIG. 15 is a perspective view of a bioabsorbable element of the present invention with its absorption profile modified by application of a coating or covering.

FIG. 15 is a schematic illustrating a further method of programming bioabsorption rates. In this embodiment, the bioabsorbable material (300) is covered with a capping layer (305). The capping layer (305) is intended to influence the degradation rate of the bioabsorbable material. A variety of bioabsorbable and non-absorbable materials may singly, or in combination, comprise the capping layer (305). Although other covering materials are contemplated, ePTFE is a wise choice due to its inherent biocompatibility and wide range of available microstructures. The covering may be in the form of a tape or film, which is wrapped upon or laminated to the bioabsorbable substrate or may be in the form of tubing, which may be pulled upon the bioabsorbable substrate. Delaying onset of bioabsorption is a function of the exclusion of water from the bioabsorbable polymer. The thicker the covering layer, or the tighter the microstructure, the longer the onset of bioabsorption will be delayed.

Figure 16:
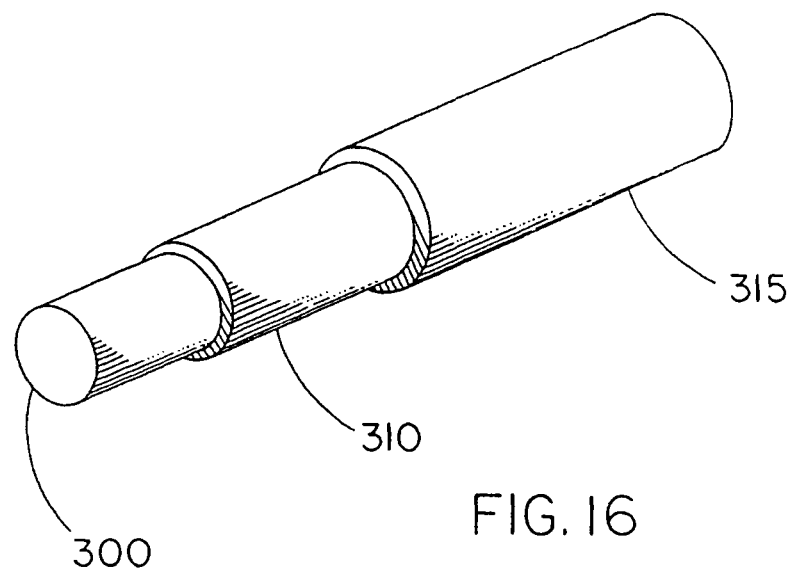
FIG. 16 is a perspective view of a bioabsorbable element of the present invention with its absorption profile modified by application of a series of coatings or coverings.

FIG. 16 shows the bioabsorbable material (300) covered with two layers of a covering material (310) and (315). These two separate layers may be of different covering materials or of the same material with different properties. It should be noted that coverings may be combined with geometrical variations (tapered struts, etc) as shown in FIG. 14 as well as with altering copolymer ratios as described in FIG. 13.

It is apparent that a bioabsorbable implantable device would be well suited as a vehicle to deliver a therapeutic agent. There are many techniques to allow a "programmed rate of bioabsorption" of a bioabsorbable material that would serve to carefully control the release of bioactive agents, such as palliatives, therapeutics, and cures in the form of bio-active pharmaceuticals, chemo-toxins, anesthetic agents, radio-isotopes, energy absorbing particles (for subsequent stimulation by MRI, ultrasound, microwaves, etc, or even additives to enhance radiopacity, MRI visibility or echogenicity.

Figure 17:
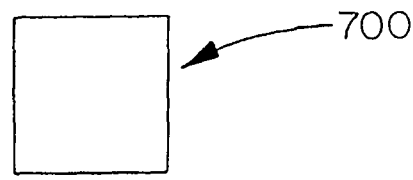
FIG. 17 illustrates as cross-sectional view of a single framework element the present invention.
Figure 18:
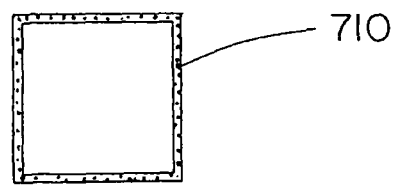
FIG. 18 illustrates a cross-sectional view of a single framework element of the present invention having a coating layer incorporating a bioactive agent in the coating layer.
Figure 19:
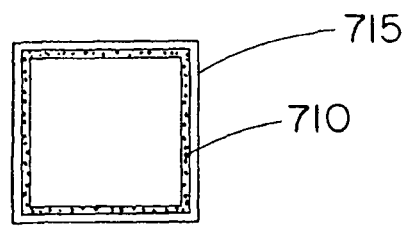
FIG. 19 illustrates a cross-sectional view of a single framework element of the present invention having a "capping," or covering, layer placed on the framework element with a bioactive agent incorporated in the capping layer.
Figure 20:
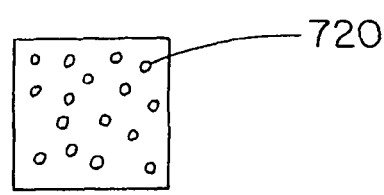
FIG. 20 illustrates a cross-sectional view of a single framework element of the present invention having a bioactive agent incorporated in material of the framework element.

Referring to FIGS. 17 and 18, one or more portions of the present invention (700) may be coated with a layer of a bioabsorbable material (710), which contains the therapeutic agent (shown as dots). FIG. 19 illustrates a capping layer (715) covering and protecting layer (710), primarily during placement in a body conduit of an implant recipient. The capping layer can also serve as means to delay onset of bioabsorption and release of the bioactive agent following implantation. FIG. 20 illustrates an embodiment of the present invention having bioactive agents (720) placed in the bioabsorbable material of the invention.

Figure 21:
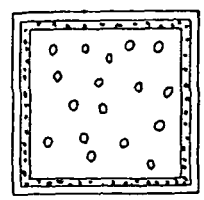
FIG. 21 illustrates a cross-sectional view of a single framework element of the present invention having a bioactive agent incorporated in material of the framework element and a coating layer. A capping layer is placed over the coating layer.
Figure 22:
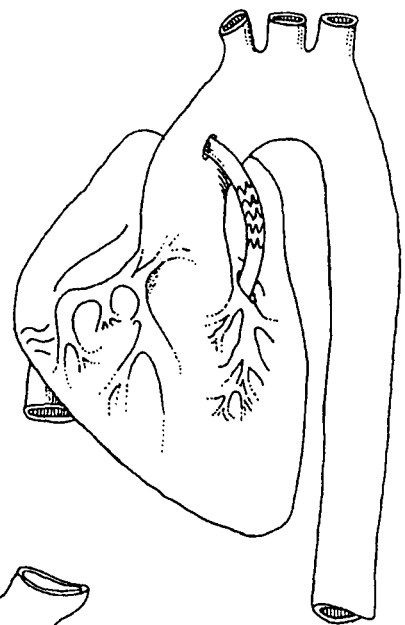
FIG. 22 illustrates an embodiment of the present invention placed outside a body conduit.
Figure 23:
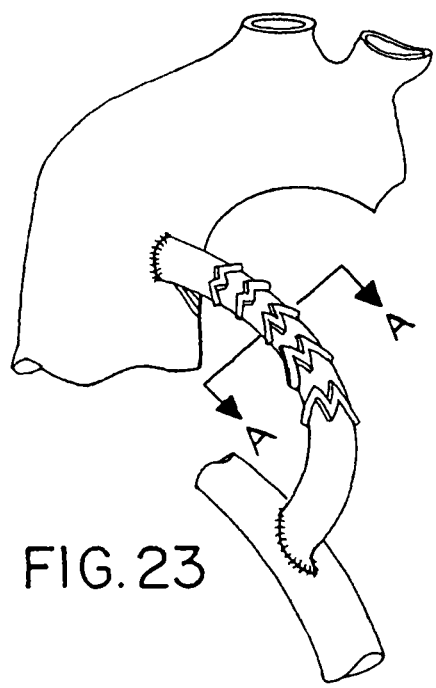
FIG. 23 illustrates a close-up of the illustration of FIG. 17.
Figure 24:
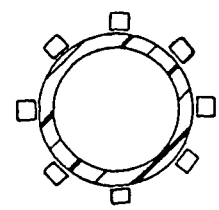
FIG. 24 is a cross-sectional view of the invention as illustrated in FIG. 18 at location A-A.

It should also be noted that combinations of the above may prove especially useful. FIG. 21 illustrates combinations of the embodiments illustrated in FIG. 18-20 in a single construction. Combinations of bioactive agents can used in the present invention. For example, a first bioabsorbable layer having antibiotic agents could reduce or eliminate infection at the implantation site, while a second layer having anti-proliferative properties could programmed to bioabsorb next. Anti-thromobotic agents could be used throughout the framework of the device.

Figure 25:
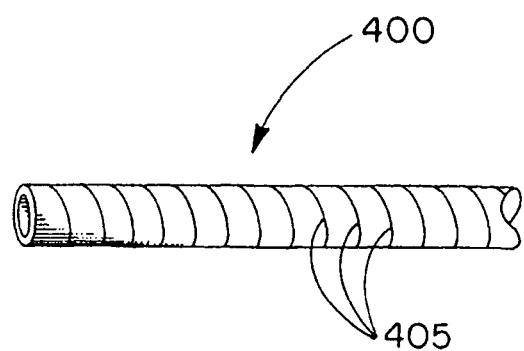
FIG. 25 illustrates a side view of a self-expandable bioabsorbable occlusion device.
Figure 26:
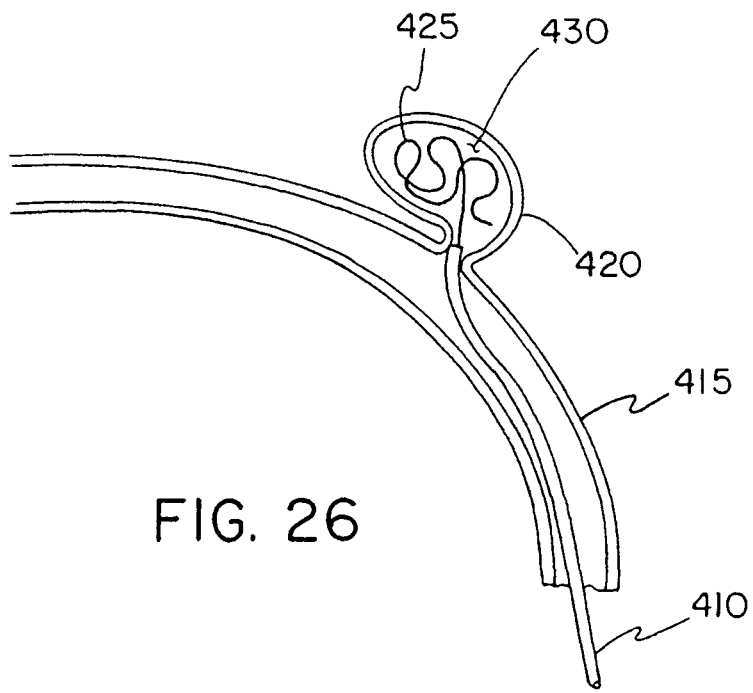
FIG. 26 illustrates placement of a delivery catheter at an aneurysmal opening and deployment of a self-expandable bioabsorbable occlusion device into the aneurysm.

Another embodiment of the present invention is illustrated in FIGS. 25 and 26. FIG. 25 shows a tube (400) made from bioabsorbable material that has been cut (405) in a spiral fashion. This spiral cut (405) imparts flexibility to an otherwise rigid tube. The spiral cut may be altered in as far as cut width (kerf), and/or pitch angle to produce variations, transitions and degrees of flexibility. The spiral cut is particularly advantageous in that the tube, even though quite flexible, will retain most of its column strength. Of course, the cut (405) need not be spiral or continuous in configuration. A perforation or a series of perforations through or even partially through the wall may be all that is required to impart the desired characteristics for the particular application. It should also be noted that many types of cutting processes may be used including, but not limited to: laser, water-jet, stamping, conventional milling and drilling, ultrasonic, etc. FIG. 26 shows the tube (400) of FIG. 25 configured for use as a neurovascular aneurysm occlusion device. In use, delivery catheter (410) is tracked through the vasculature (415) and accesses the mouth of an aneurysm (420). The bioabsorbable occlusion coil (425) is then advanced from the catheter (410) and into the aneurysmal compartment (430) where it randomly organizes and induces thrombosis within the aneurysm (420). The coil of this embodiment may also be imparted with various accessories such as fibers, fuzz or therapeutic agents intended to stimulate thrombosis.

Figure 27:
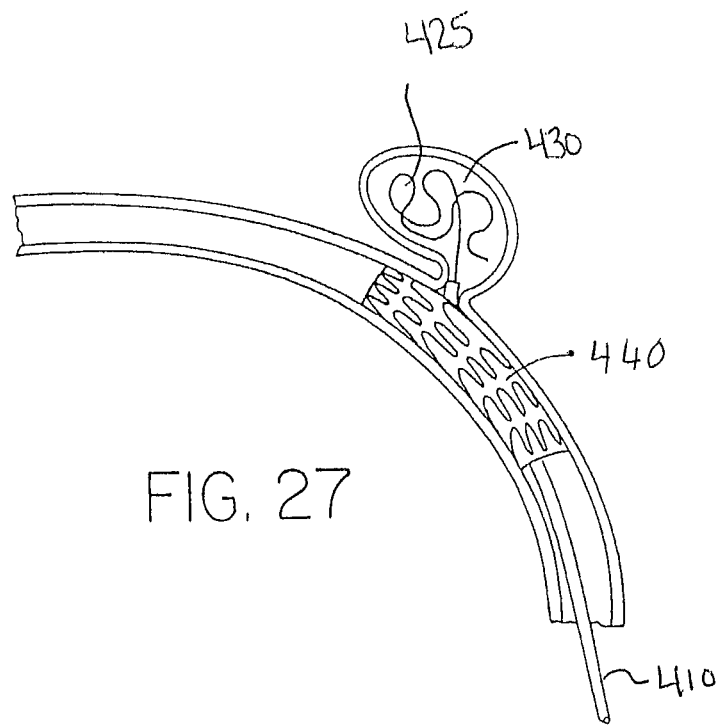
FIG. 27 illustrates placement of a delivery catheter through a port in a stent-graft at an aneurysmal opening and deployment of a self-expandable bioabsorbable occlusion device into the aneurysm from the catheter.
Figure 28:
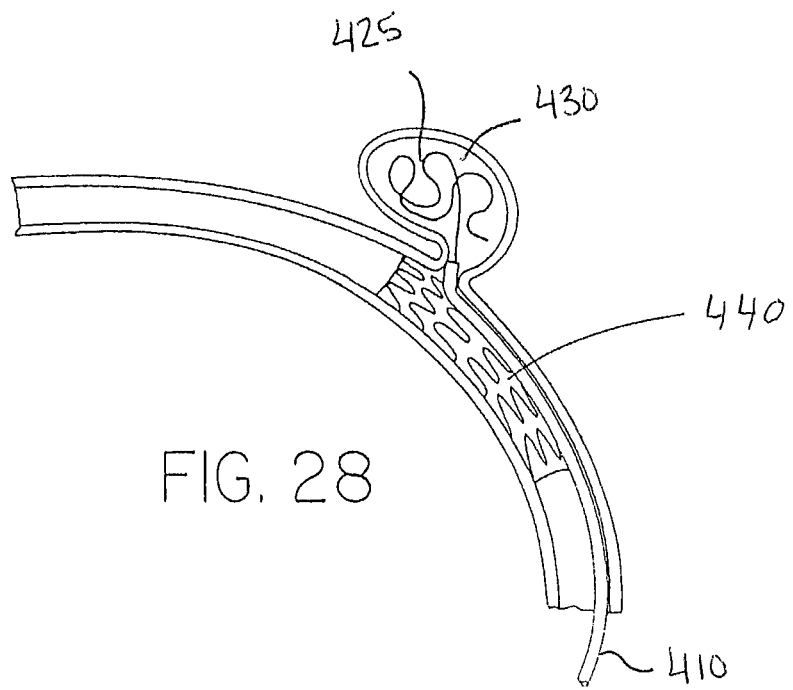
FIG. 28 illustrates placement of a delivery catheter next to a stent-graft at an aneurysmal opening and deployment of a self-expandable bioabsorbable occlusion device into the aneurysm from the catheter.

It should also be noted that the occlusion coil (425) could also be used in conjunction with a stent or stent graft. FIGS. 27 and 28 depict the occlusion coil (425) in use in such a fashion. A stent or stent-graft may be particularly useful in this application when the aneurysm has a wide mouth or opening. In such a case, there may be risk of occlusion coil (425) not seating properly or tending to sag out of the aneurysmal space and enter the vessel lumen. A stent or stent graft can assist in holding the occlusion coil in place until the aneurysm clots closed. The stent and/or stent graft may be conventional (self-expanding or balloon expandable metallic) or may also be made of a bioabsorbable material.

EXAMPLES

Example 1

This example describes the preparation of an extrudate made of a bio-absorbable polymer suitable for use in the present invention. The extrudate is subsequently extruded into a tubular shape for further processing into a device of the present invention.

A tri-block co-polymer of poly(glycolide) and poly(trimethylenecarbonate) having a weight to weight (w/w) ratio of 67% poly(glycolide) to 33% poly(trimethylenecarbonate) was acquired from Davis and Geck/United States Surgical (Manati, Puerto Rico—Lot #:01101). This bioabsorbable PGA/TMC co-polymer, commonly referred to as polyglyconate, was provided with certification to its co-polymer ratio.

Upon receipt, approximately 25 mg of the PGA/TMC co-polymer was dissolved in 25 ml of hexafluoroisopropanol (HFIP). The produced dilute solution was found to possess an inherent viscosity (IV) of 1.41 dl/g when measured using an AUTOVISC™ I automated viscometer operating at 30 degrees centigrade.

Approximately 6 mg of the acquired PGA/TMC co-polymer was placed into an aluminum Differential Scanning Calorimetry (DSC) sample pan, covered, and analyzed utilizing a Perkin-Elmer DSC 7 equipped with an Intracooler II cooling unit able to provide sample cooling to temperatures as low as −40 degrees centigrade. The sample was cooled and scanned from −40 degrees centigrade to 250 degrees centigrade at a scanning rate of 10 degrees centigrade per minute.

The sample was found to possess a glass transition temperature (Tg) of approximately eleven (11) degrees to twelve (12) degrees centigrade.

After completion of this initial scan, the PGA/TMC co-polymer sample was maintained at 250 degrees centigrade for 5 minutes and then immediately cooled at the maximum rate provided by the instrument. A second similar scan was undertaken on the same sample over the same temperature range. Each scan was analyzed for the $T_g$ or $T_{odt}$, observed crystallization exotherm, and melt endotherm. The results are summarized in the following table.

|  | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | 13.8° C. | 0.49 J/g*° C. | none | None | 212.8° C. | 42.0 J/g |
| Heat 2 | 17.4° C. | 0.72 J/g*° C. | 106.2° C. | −35.2 J/g | 206.3° C. | 39.1 J/g |

The above results were found to be indicative of a semi-crystalline copolymer system possessing a glass transition temperature well below both normal human body temperature (i.e. 37° C.) and room temperature (i.e. 20-25° C.) conditions. The order-disorder transition temperature (representative of a homogenous uncrystallized copolymer system) of 17.4° C. was near the 17.2° C. predicted by the Fox equation assuming the Tg for PGA homopolymer to be 36° C. and the Tg for TMC homopolymer being −15° C.

Example 2

This example describes the formation of a construction of a bioabsorbable polymeric material suitable for further processing into a device of the present invention. The construction was extruded into a tubular shape with a 0.5 inch, 24:1, screw extruder (Randcastle Extrusion Systems, Inc., Cedar Grove, N.J.). The extruder had a three-stage screw.

The process was begun by heating approximately 200 grams of the PGA/TMC block co-polymer of Example 1 overnight under vacuum at 130 degrees centigrade to dry the co-polymer. The dried co-polymer was then placed into the extruder.

The extruder was programmed to provide a temperature profile that achieves a melt temperature between 205 degrees and 210 degrees centigrade with a die temperature between 205 degrees and 210 degrees centigrade. The extruder melted and pumped the polymer through a Genca (Clearwater, Fla.) tubing die designed to produce a draw ratio of about 5:1 with a draw ratio balance of about 1.00.

The extruded tube was pulled through a cooling trough using a nip roll capstan and was cut into pieces about twelve (12) inches long. Due to the very slow rate of recrystallization of the PGA:TMC co-polymer, the tube was in an amorphous, or disordered state, and care was taken not to distort the soft extrudate.

The cut tubes were refrigerated at a temperature below 16 degrees centigrade, (i.e., below the order-disorder transition temperature (Todt) of the co-polymer) in order to allow the polymer to be handled in the glassy or more rigid state. The tubes were then carefully forced onto a mandrel having an outer diameter substantially equal to the inner diameter of the finished tubular device.

The mandrel and tube were then placed in an oven set at 100 degrees centigrade for 15 minutes. This allowed the polymer to crystallize and take the form of the mandrel.

Example 3

This example describes forming fenestrations (14) in the tubular construction (16) of Example 2 with an excimer laser. When the fenestrations were formed in the construction, a device of the present invention (10) comprising an integral self-expanding, non-elongating, bioabsorbable framework (12) was formed. The finished device once sterilized can serve as a bioabsorbable support for a body conduit.

A 248 nm gas excimer laser (available from J. P. Sercel Associates, Inc., Hollis, N.H., system JPSA 100-01-INV024, model IX1000) was used to form a series of fenestrations (14) in the tubular construction (16). The laser was set to produce a 110 milli-joules light beam, repeatedly pulsed at 200 Hz. The energy density at the device was 2 Joules per square centimeter.

The laser was fitted with attachments that permitted a chuck for holding and rotating a mandrel to be attached to the laser. The chuck was driven by a rotary servomotor. A base tube for a device of the present invention was placed over the mandrel and prepared to be rotated in concert with movement of an aperture mask and pulsing of a controlled beam of laser energy to cut the fenstrations (14).

Figure 8:
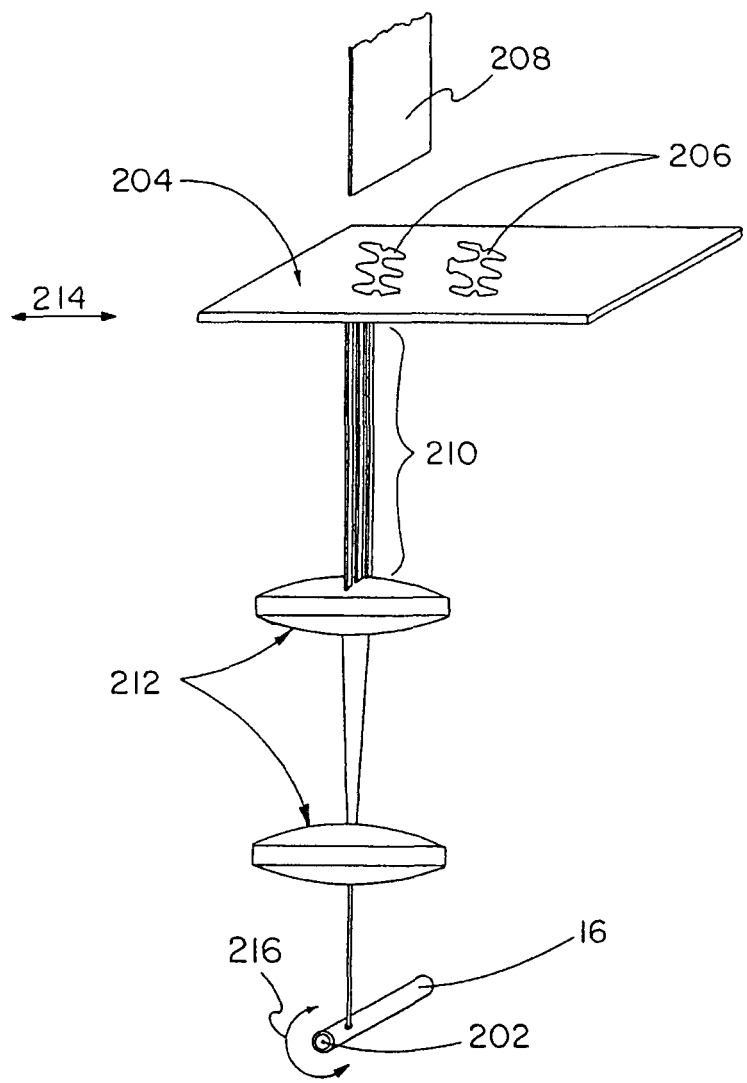
FIG. 8 is a generalized schematic illustrating the relationship of manufacturing equipment with a device of the present invention.

FIG. 8 illustrates the relative placement of the manufacturing components and the tubular construction of this example. Cutting fenestrations (14) was begun by obtaining a tubular construction (16) as described in Example 2 and cutting the construction to a length greater than the final desired length of the invention. The construction (16) was initially placed over a stainless steel mandrel (202). The mandrel (202) was secured in the chuck component (not shown) of the laser apparatus (not shown) and positioned for rotation in the apparatus.

Figure 2:
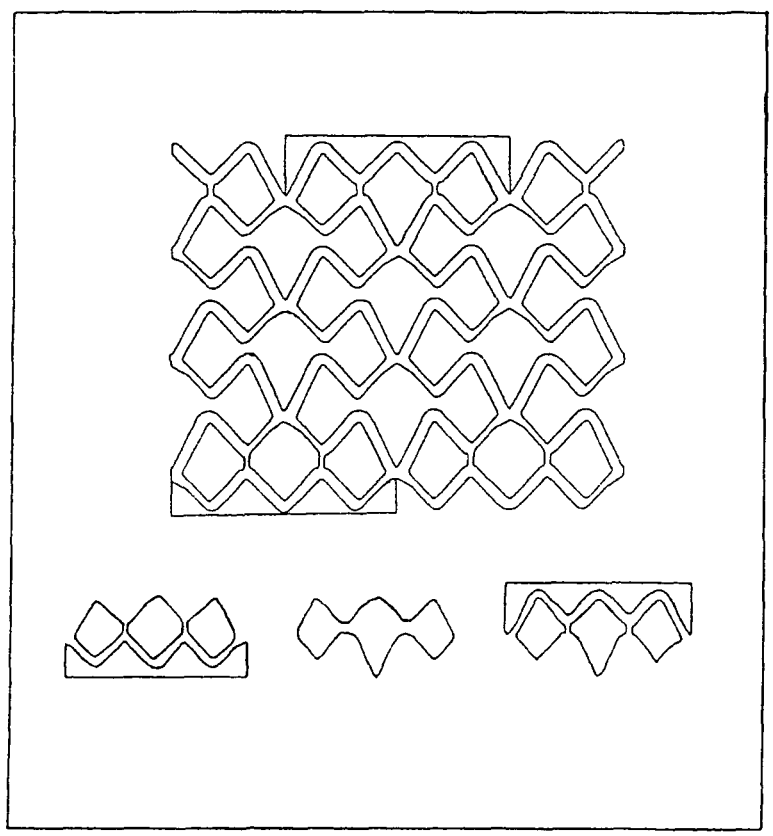
FIG. 2 illustrates an aperture-containing mask for use in laser-cutting fenestrations in the present invention.
Figure 3:
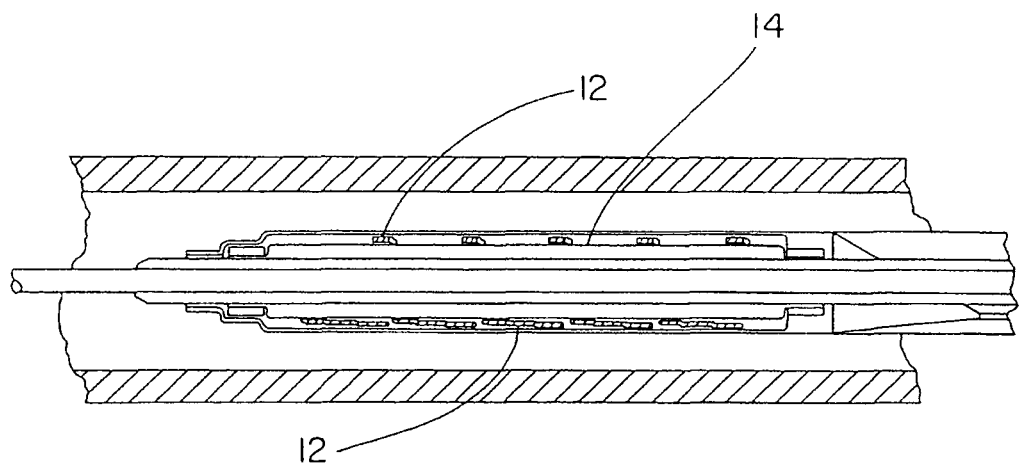
FIG. 3 illustrates a cross-sectional view of a device of the present invention in a radially compressed configuration.
Figure 4:
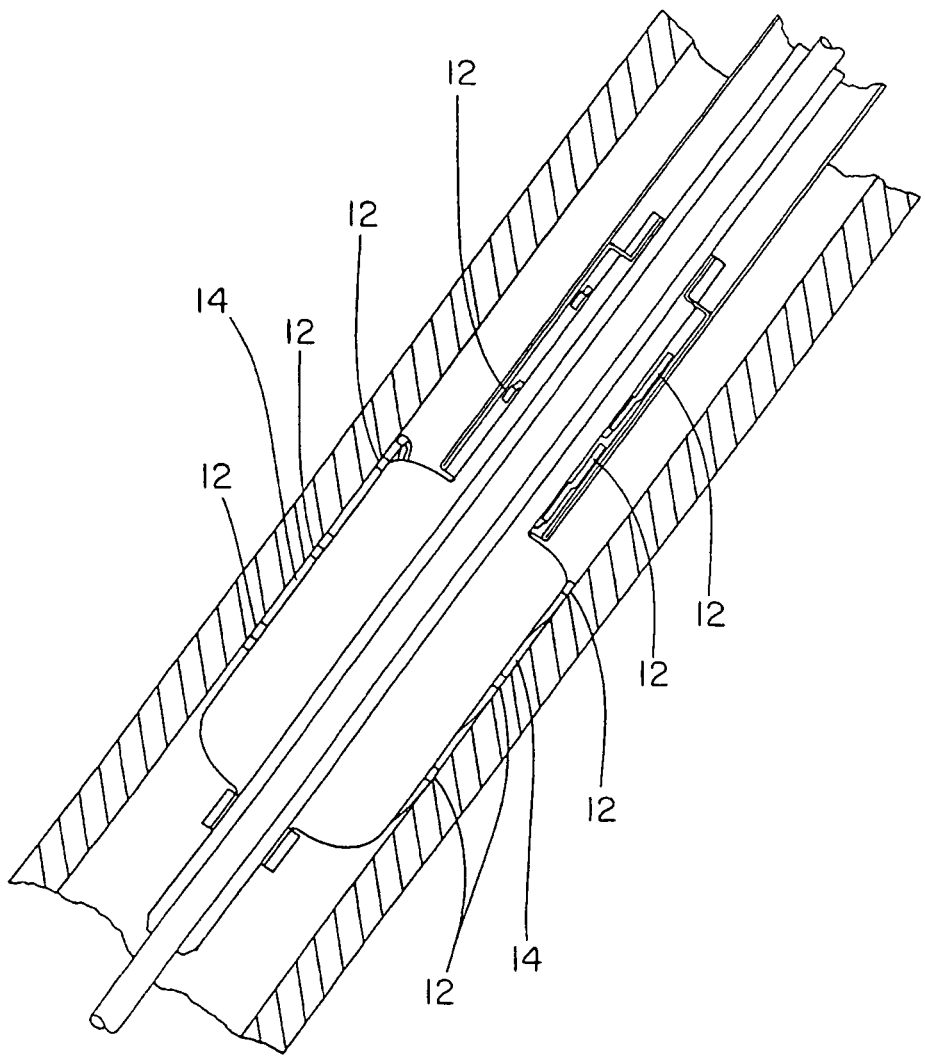
FIG. 4 illustrates a cross-sectional view of a device of the present invention having a portion in a radially compressed configuration and a portion in an expanded configuration.
Figure 5:
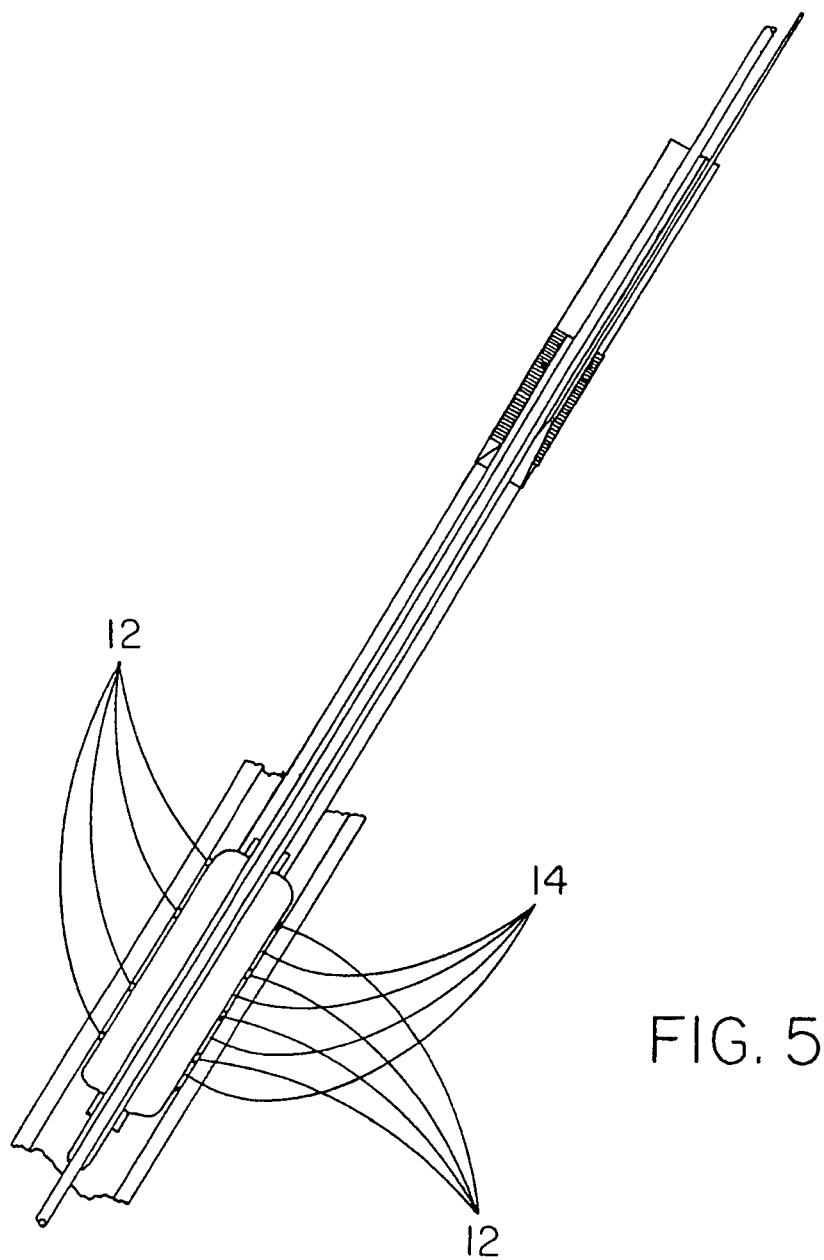
FIG. 5 illustrates a cross-sectional view of a device of the present invention in a radially expanded configuration.

The manufacturing equipment (not shown) was configured with a movable laser-cut 0.020 inch thick stainless steel mask (204) having a series of apertures (206) in the shape of the intended fenstrations (FIG. 2). An excimer laser beam (208) was first optically expanded to fill a rectangularly shaped aperture mask. The beam (208) was passed through the apertures (206) of the mask to form a series of narrow rectangularly-shaped laser "beamlettes" (210). The beamlettes were focused onto the tubular construction. The long axis of the rectangular beamlettes was greater than the largest mask aperture measured in the non-scanning direction. The short axis of the rectangular beamlettes was determined by the amount of laser energy needed to minimize heat in the zone of the beamlettes and to minimize processing time.

To determine how much greater the size of the apertures (206) was than the fenestrations (14), the amount by which the apertures needed to be increased in size beyond the dimensions of the fenestrations was equal to a demagnification ratio of the downstream beam delivery system. The demagnification ratio, in this example, was 5:1. The density of the laser energy required cut fenestrations in the tubular construction (16) was a major factor in determining this ratio. The demagnification ratio provides a resolution advantage between the aperture mask and device and simplifies the mask manufacturing requirements, especially for small device features. Adjustment to the beamlettes was accomplished with an array of "de-magnification" optics (212).

To form each fenestration, the excimer laser was pulsed fifty (50) times per unit area with forty (40) microns of device movement between each pulse. These pulsed beamlettes were passed over each fenestration area ten (10) times. The laser was activated as the mask oscillated (214) in a plane parallel to the short axis of the rectangular laser beam. In turn, the mandrel was precisely rotated (216) about its own cylindrical axis in coordination with the oscillating mask (204, 214). This coordinated motion replicates the mask aperture geometry onto the continuously curving surface of the tubular construction (16) and enables an even application of laser energy to be applied. Laser energy is applied to the construction until the desired amount of material is ablated from the area defined by the mask apertures. This even application of laser energy resulted in precise, repeatable, ablation of the bioabsorbable material of the construction (16).

The mandrel (202) and mask (204) were then repositioned in a coordinated manner, indexed, and another fenestration (14) formed in the construction (16). The process was repeated until fenstrations were formed in the tubular bioabsorbable construction along the entire length and circumference of the construction (FIG. 1). The same process was used with a different mask to cut both ends of the construction.

When all the fenestrations were formed and the ends finished, the construction removed from the mandrel. Prior to removing the device from the mandrel, the cut piece was rinsed in isopropyl alcohol to solvent-crystallize any heat-affected material. A device of the present invention was thus formed that is suitable for use as an implantable bioabsorbable device for a body conduit. The bioabsorbable device radially expands from a compressed first diameter to an unrestrained second diameter equal to or greater than 1.5 times said first diameter within two minutes following immersion in an aqueous medium at 37 degrees centigrade without requisite for an extrinsically applied force and without requisite for a thermal transition.

Figure 6:
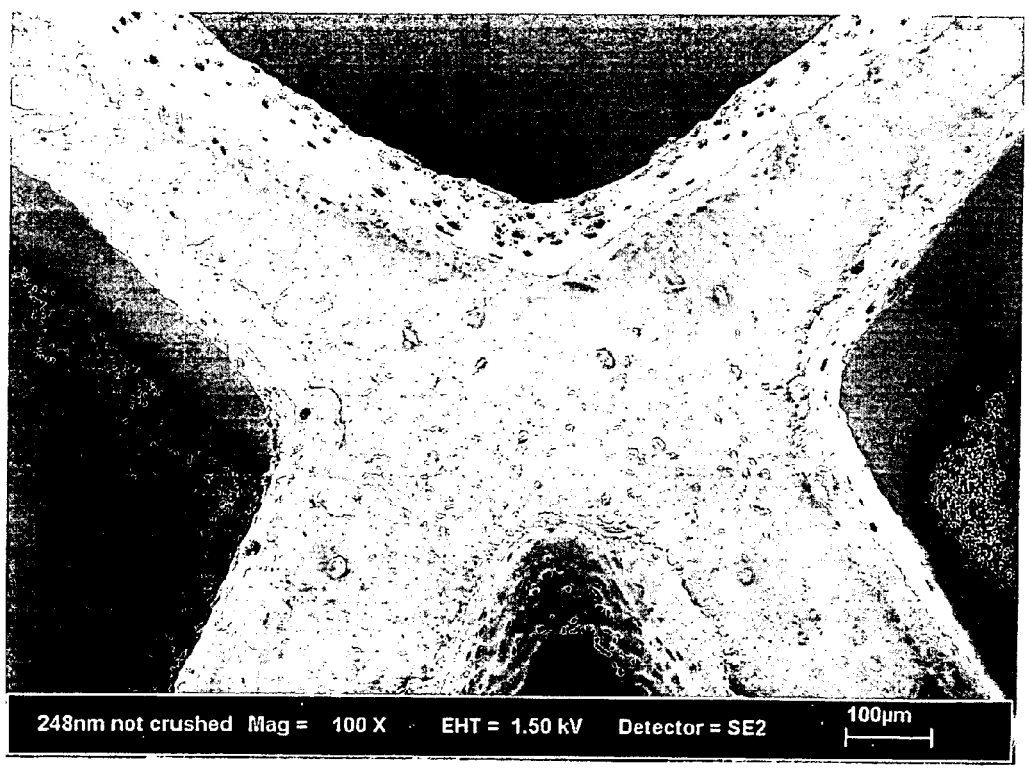
FIG. 6 is a scanning electron micrograph showing a portion of an integral framework of the present invention formed with an excimer laser.

It is noteworthy that this excimer laser cutting process produces fenestrations delimited with border material having pits, holes, cavities, or other subsurface features (FIG. 6). These features can be used as an aid in attaching a coating to the integral framework of the invention. The features can also serve as reservoirs for bioactive compounds and entities. The reservoirs can also contain fillers, such as radiopaque elements or compounds. The compounds or entities can be released from the features as the bioabsorbable material of the invention undergoes bioabsorption. Alternatively, the bioactive compounds and/or entities can be released independent of the bioabsorption of the invention. The bioactive compounds can also be incorporated into coatings applied to surfaces of the present invention.

Alternatives and variants of this construction are produced by routine testing and optimization of the equipment and materials used to make a device of the present invention.

Example 4

This example describes forming fenestrations (14) in a tubular construction (16) made of a bioabsorbable polymer having a glass transition temperature less than thirty-seven (37) degrees centigrade with a carbon-dioxide laser. When the fenestrations were formed in the construction, a device of the present invention (10) comprising an integral self-expanding, non-elongating, bioabsorbable framework was produced. The finished device once sterilized can serve as a bioabsorable support for a body conduit.

An approximately 25 mm (1.0 inch) long tubular construction (16) of Example 2 having an inner diameter of 4.0 mm was placed over a 51 mm (2 inch) long stainless steel mandrel having an outer diameter sized to provide a snug fit with the tubular construction.

Figure 7:
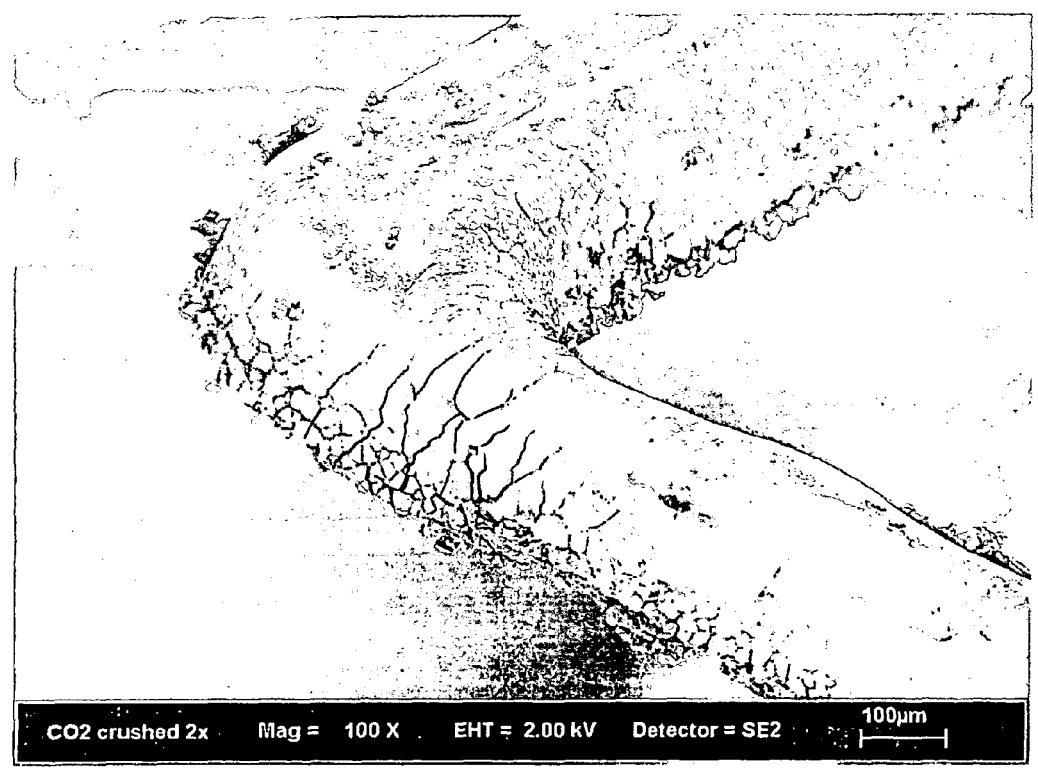
FIG. 7 is a scanning electron micrograph showing a portion of an integral framework of the present invention formed with an carbon dioxide laser.

A bare end of the mandrel was placed in a rotatable chuck. The chuck and rotary stage were used in concert with a 30 watt carbon dioxide laser (Model 30A, Coherent, Inc., Santa Clara, Calif.). A computer program written in Visual Basic containing instructions for cutting the fenestration pattern shown in FIG. 1A was entered into the laser cutting machine and the fenestration pattern was cut into the tubular construction according to the program. The pattern was cut with a series of linear passes of the laser that outlined the intended shapes of the fenestrations. A scanning electron micrograph of a portion of the integral framework thus produced is shown in FIG. 7.

The mandrel along with the newly formed fenestrated tubular construction was removed from the chuck and placed in an oven set at one hundred degrees centigrade (100° C.) for seven (7) to ten (10) minutes to re-set, or recrystallize, any heat affected polymer material on the laser-cut piece. The mandrel and the construction were removed from the oven and cooled with chilled air to between four (4) degrees centigrade (40° F.) and fifteen (15) degrees centigrade (60° F.).

When all the fenestrations were formed, the ends finished, and the construction removed from the mandrel, a device of the present invention was formed that is suitable for use as an implantable bioabsorbable device for a body conduit. The bioabsorbable device radially expands from a compressed first diameter to an unrestrained second diameter equal to or greater than 1.5 times said first diameter within two minutes following immersion in an aqueous medium at 37 degrees centigrade without requisite for an extrinsically applied force and without requisite for a thermal transition.

To facilitate the loading of the device into a delivery catheter or other constraining member, the device can be radially compressed to a diameter smaller than the inner diameter of the constraining member. While in the compressed state, the device can be chilled to about minus fifteen degrees centigrade (−15° C.), for example. The chilled device can then be removed from the compression die and quickly loaded into the delivery catheter. The reduced temperature delays the "self-expansion" of the device so that the device temporarily remains in the compressed state.

Example 5

This example describes application of a bioabsorbable coating to a device of the present invention. The coating can add structural integrity or other mechanical properties to the invention. Bioactive compounds or entities can also be included in the coating and released as the coating undergoes bioabsorption.

A fenestrated tubular construction made according to Example 3 was obtained and the surfaces of the construction coated with bioabsorbable poly(d,l-lactide-co-trimethylene carbonate) copolymer in weight percent ratio of 80:20 (80% d,l-PLA:20% TMC) in a chloroform solvent. Synthesis of a broad variety of d,l-PLA:TMC copolymers is detailed within U.S. Pat. No. 5,610,266, assigned to Boehringer Ingelheim KG, and incorporated herein by reference. The coating solution was comprised of (0.48 wt %) 80% d,l-PLA:20% TMC (IV in $CHCl_3$ at 30° C., ~5.0 mg/ml=0.63 dl/g) in chloroform.

Approximately 2.0 ml of the solution was sprayed at the construction with an air atomizing nozzle. The nozzle was maintained 25 mm from the construction as it was rotated at approximately 30 rpm. The solution was applied at a rate of 0.5 ml per minute.

The spray-coated construction was heated at 125 degrees centigrade for ten (10) minutes to remove residual chloroform solvent.

The resultant coating was found to be tenaciously attached to the bio-absorbable construction. Indeed, scanning electron micrographs (SEM) of the coated construction did not show a distinct demarcation line between the construction and the coating.

Example 6

This example describes the coated construction of Example 5 having a pharmaceutical agent incorporated into the coating for release at an implantation site.

The coating solution was prepared as described in Example 5 with the addition of (0.3 wt %) of the anti-inflammatory and anti-proliferative compound dexamethasone (Pharmacia Upjohn).

The dexamethasone-containing coating solution was applied the same way as the non-drug containing coating described in Example 5.

A top coat of the non-drug containing solution was applied to the drug coated stent per the conditions outlined in Example 5.

Here too, the drug and non drug-containing coatings were found to be tenaciously attached to the bio-absorbable construction when examined under a scanning electron microscope (SEM).

The resulting bio-absorbable construction was an integral framework delimiting a multiplicity of fenestrations. The framework comprises a non-blended hydrolyzable polymeric material in combination with a bioactive compound. The framework was substantially tubular in shape.

When the bio-absorbable construction was compressed onto a delivery catheter, the construction radially expanded from a compressed first diameter to an unrestrained second diameter equal to or greater than 1.5 times said first diameter within two minutes following immersion in an aqueous medium at 37 degrees centigrade. The construction radially expanded without requisite for an extrinsically applied force and without requisite for a thermal transition of the bio-absorbable polymeric material. No evidence of cracks or other defects in the coating was observed following compression and expansion of the invention.

Example 7

This example describes implantation of the construction of Example 3 in an animal model. In this study, both carotid arteries of three (3) greyhound dogs were implanted with devices of the present invention described in Example 3. Animals received antiplatelet medication consisting of a daily oral dose of 81 mg aspirin and 50 mg of dipyridamole beginning three days prior to implant of the construct and continuing throughout the in life period of the study. The constructions were approximately 4.7 mm in diameter and 20 mm long. Radiopaque crimp tubes were added to both ends of the construction to provide a means of radiographic imaging the construction in vivo. The constructions were compressed (via crimping and chilling to −15° C.) and introduced into a conventional endovascular delivery catheter, packaged in a suitably sized sterilization pouch, and sterilized by gamma radiation (~25 kGy). Using interventional radiographic techniques, the constructs were delivered and deployed to the implantation site by one of two methods. Method one was to position the distal end of the delivery catheter at the vascular target site and, while holding the delivery catheter in place, inserting an angiographic catheter of appropriate size into the lumen of the delivery catheter and pushing the construct from the delivery catheter using the angiographic catheter as a plunger. Method two was to position the distal end of the delivery catheter at the vascular target site and, while holding the construct in place with the angiographic catheter, retracting the delivery catheter thus deploying the construct at the vascular target site.

Angiographic imaging of the implanted constructs, performed at approximately 18, 39, 90, and 180 days, showed that all constructs remained patent throughout the 180-day evaluation period. Though, histologically, residuals of the construct material were present in some cases; essentially all of the constructs were completely absorbed by 180 days.

Example 8

This example describes the self-expanding properties of the present invention. A tubular self-expanding device of the present invention radially expands from a compressed first diameter to an unrestrained second diameter equal to or greater than 1.5 times said first diameter within two minutes following immersion in an aqueous medium at 37 degrees centigrade without requisite for an extrinsically applied force and without requisite for a thermal transition.

To demonstrate these features a device of the present invention was prepared according to Example 3. The device was approximately 1.0 cm in length with a wall thickness of about 0.178 mm and an inner diameter of 3.5 mm. The device was compressed to a first diameter of 1.91 mm and restrained. The compressed device was immersed in water at 37 degrees centigrade. No extrinsically applied force was applied to the device during the demonstration (i.e., the device was not expanded with a balloon or any other device). Within a two minute time period, the device expanded to an unrestrained diameter of at least one and a half (1.5) times greater than the first compressed diameter in the heated water bath. The properties of the non-blended hydrolyzable polymeric material from which the device are such that a thermal transition of the material was not required in order for the device to expand from the first compressed diameter to the second unrestrained diameter.

Example 9

This example describes the test performed to characterize the tensile properties of a device of the present invention and the results of this characterization.

A device of the present invention was prepared according to Example 3 and clamped in a calibrated INSTRON™ tensile testing apparatus (Instron Corp., Canton, Mass., model 5564). The device was clamped in a vertical orientation, with the long axis of the tubular device parallel to the direction of crosshead displacement. The initial jaw separation was 6 mm, with approximately 2 mm of the device clamped in each grip. A 6 mm initial jaw separation was used in engineering strain calculations. A crosshead speed of 10 mm/min was employed. Data consisting of tensile load and extension were gathered at one second intervals. This evaluation was intended to characterize the axial expansion tensile strength of the device.

Figure 1A:
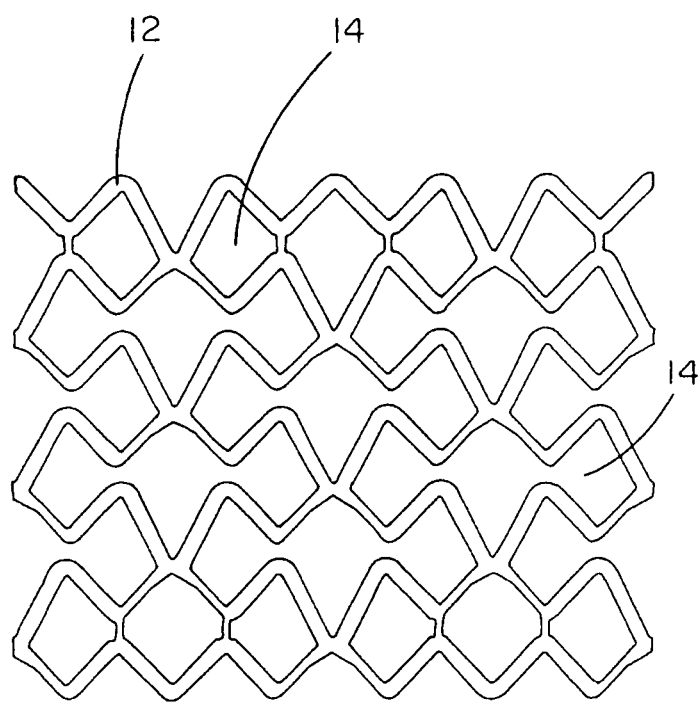
FIG. 1A illustrates a section of the integral framework of the present invention having a multiplicity of fenestrations.

From the data, engineering strain and engineering stress were calculated. Engineering stress calculations were based on the cross-sectional of the narrowest device struts (FIG. 1A). As the device is axially deformed, the minimum cross-sectional area (based on a plane perpendicular to the long axis of the device) is defined by the cross sectional area of four of the said narrow struts. These struts are nominally 0.178 mm (0.007") in width, and the nominal wall thickness of the device is also 0.178 mm (0.007").

This example describes the test performed to characterize the tensile properties of a device of the present invention and the results of this characterization.

A device of the present invention was prepared according to Example 3 and clamped in a calibrated INSTRON™ tensile testing apparatus (Instron Corp., Canton, Mass., model 5564). The device was clamped in a vertical orientation, with the long axis of the tubular device parallel to the direction of crosshead displacement. The initial jaw separation was 6 mm; this distance was used in engineering strain calculations. A crosshead speed of 10 mm/min was employed. Data consisting of tensile load and extension were gathered at one second intervals. This evaluation was intended to characterize the axial expansion tensile strength of the device.

From the data, engineering strain and engineering stress were calculated. Engineering stress calculations were based on the cross-sectional of the narrowest device struts (FIG. 1A). As the device is axially deformed, the minimum cross-sectional area (based on a plane perpendicular to the long axis of the device) is defined by the cross sectional area of four of the said narrow struts. These struts are nominally 0.178 mm (0.007") in width, and the nominal wall thickness of the device is also 0.178 mm (0.007"). Therefore, engineering stress calculations were based on a cross sectional area of 0.126 mm) $1.96 \times 10^{-4}$ in$^2$.

The Young's modulus of the device is defined as the slope of the stress-strain curve generated in this fashion. Two separate moduli were obtained from this experiment: that related to the axial expansion of the device and that related to the tensile strength of the constituent material. Moduli were calculated as the slope of the stress-strain curve in the linear regions related to the axial expansion of the device and then separately in the linear region related to the tensile properties of the device constituent material. The moduli calculated in this fashion were 2.1 MPa for the axial expansion of the device, and 24.1 MPa for tensile loading of the constituent material.

Example 10

This example describes placement of a non-bioabsorbable covering on the construction of Example 3.

A device according to Example 3 was obtained as describe above. A porous expanded polytetrafluoroethylene (ePTFE) film material was made according to U.S. Pat. Nos. 3,953,566 and 4,187,390, both issued to Gore and incorporated herein by reference.

The two components were attached by coating the interface surfaces with a solution of polylactic acid—polyglycolic acid (PLA:PGA) in a mole ratio of 85:15, respectively which was rendered into liquid form by dissolving in acetone. Once the surfaces were coated, the film was helically wrapped around the device to substantially cover the fenestrations. The components were pressed and held together until under pressure. The assembly was allowed to dry overnight. The result was a stent-graft of the present invention.

Example 11

This example describes placement of a bioabsorbable covering on the construction of Example 3.

An approximately 4 mm (I.D.) device fabricated as generally described in Example 3 was obtained. An approximately 0.1 to 0.2 mm thick section of bioabsorbable web material based on the teachings in U.S. Pat. Nos. 6,165,217 and 6,309,423, both issued to Hayes and incorporated herein by reference, was also obtained.

An approximately one inch wide section of "unset" (i.e. un-annealed) bioabsorbable web material was longitudinally wrapped lengthwise ("cigarette-wrapped") over an appropriately sized stainless steel mandrel, overlapped by approximately 0.3 cm, and secured by limited thermal point bonding. The device of Example 3 was then manipulated to both overlay and apply light compression to the underlying web. An additional layer of unset web was then wrapped over the combination in a helical overlapping fashion and then secured so as to apply light compression to the underlying stent while substantially its fenestrations. The combination was then wrapped in a helical fashion with a strip of e-PTFE and then secured to effect both restraint and compression through the fenestrations of the assembly.

The mandrel and overlying components were then heated at 100° C. for 30 minutes and then allowed to cool. It was found that the lumenal positioned web was now—through the fenestration voids of device provided in Example 3—cohered to the ablumenal positioned web. The result was a stent-graft of the present invention composed entirely of a single 67% PGA:33% TMC bioabsorbable composition. The now integrated assembly was found to readily return to the stent graft's original tubular configuration after tactile application of compressive force.

Example 12

This example describes the construction of a self-expanding stent-graft having a metallic framework and a bioabsorbable covering on the framework.

A bioabsorbable stent graft was constructed by winding a helical 4 mm diameter nitinol stent frame over a mandrel covered by a layer of "unset" non-woven web prepared in a manner consistent with the methods described in U.S. Pat. Nos. 6,165,217 and 6,309,243, followed by both coverage with an additional unset web layer and thermal annealing. The unset web layers utilized in the construction were prepared from a 67% PGA:33% TMC copolymer similar to that described in preceding Example 1 (except using D&G/USS Lot #04F04), with the first web layer cigarette-wrapped and thermally point bonded around a 3.45 mm mandrel covered with a 0.076 mm (0.003 inch) e-PTFE cushion tube. The web was then overlayed with a 30 mm long helical coil constructed from a single 0.152 mm (0.006 inch) diameter nitinol wire imparted with an underlying repeating zig-zag pattern. The final unset web layer was then applied by wrapping a strip of the web around the loaded mandrel followed by immobilization with an additional wrap of e-PTFE tape both to secure the top web layer and to provide compression to the underlying layers. The combination was then placed into an oven at 100° C. for 15 minutes to assure a "set" or annealing of the PGA:TMC web components. The result observed upon removal was a 0.203 mm (0.008 inch) wall thickness non-woven stent graft with an embedded helical nitinol spine that imparted ready return to the stent graft's original tubular configuration after tactile application of compressive force.

The invention claimed is:

1. A self-expanding support for a body conduit comprising:
   a substantially tubular framework delimiting a multiplicity of fenestrations;
   a filter device attached to said tubular framework, said filter device comprising:
   non-bioabsorbable frame elements; and
   bioabsorbable filter elements attached to said frame elements, wherein said bioabsorbable filter elements converge at a center region to form a generally conical structure with openings between said filter elements for fluid therethrough;

wherein portions of said filter elements at said center region of said conical structure are bioabsorbed prior to portions of said filter elements located at a periphery of said filter elements, wherein said framework is continuous, non-filamentous, non-braided, and non-interlaced;

wherein said framework is made of a non-blended hydrolysable co-polymeric material comprising an amorphous component with a glass transition temperature that is below ambient body temperature and a crystallizable component that possesses a crystalline melting point in excess of ambient body temperature; and wherein said framework expands radially from a compressed first diameter to an uncompressed second diameter below normal human body temperature without requisite for an externally applied force and without requisite for a thermal transition of said polymeric material.

2. The support of claim 1 wherein said fenestrations are laser-cut.

3. The support of claim 1 wherein said non-blended hydrolyzable co-polymeric material is a tri-block co-polymer of poly(glycolide) and poly(trimethylenecarbonate).

4. The support of claim 1 further comprising an agent combined with said polymeric material.

5. The support of claim 4 wherein said agent is a bioactive agent.

6. The support of claim 5 wherein said bioactive agent is dexamethasone.

7. The support of claim 4 wherein said agent is a non-bioactive agent.

8. The support of claim 7 wherein said non-bioactive agent is radiopaque.

9. The support of claim 1, wherein said framework comprises a different copolymer ratio than said filter elements.

10. The support of claim 1, further comprising anchors to attach said support to a vessel wall.

11. The support of claim 1, further comprising suspension elements, wherein a geometry of said filter elements is configured to hold suspension elements toward a center of luminal space of a body conduit.

12. The support of claim 1, further comprising an occlusion coil.

13. The support of claim 1, wherein said framework is made of a non-blended hydrolysable co-polymeric material comprising an amorphous component with a glass transition temperature that is below ambient body temperature and a crystallizable component that possesses a crystalline melting point in excess of ambient body temperature.

14. The support of claim 1, wherein said filter elements vary in width along their length and narrow in width toward said center region such that said portions of said filter elements at said center region are bioabsorbed prior to said portions of said filter elements located at said periphery.

15. The support of claim 1, wherein said filter elements are formed of bioabsorbable polymeric materials having differing rates of bioabsorbtion such that said portions of said filter elements at said center region are bioabsorbed prior to said portions of said filter elements at said periphery.

16. The support of claim 1, wherein said filter elements are interconnected with a plurality of concentric rings, each said concentric ring having a different rate of bioabsorbtion.

17. The support of claim 1, further comprising a capping layer on said bioabsorbable filter elements to delay the onset of bioabsorbtion of said filter elements.

18. The support of claim 17, wherein said capping layer comprises expanded polytetrafluoroethylene.

19. The support of claim 17, wherein said capping layer contains at least one therapeutic agent.

20. The support of claim 1, further comprising a capping layer on said bioabsorbable filter elements, wherein at least one of said framework, said non-bioabsorbable frame elements, and said bioabsorbable filter elements are coated with a layer of a bioabsorbable material that contains at least one therapeutic agent, and wherein said capping layer delays the release of said at least one therapeutic agent.

21. The support of claim 1, further comprising a first capping layer and a second capping layer, at least one of said first capping layer and said second capping layer containing one or more therapeutic agent.

22. A self-expanding support for a body conduit comprising:

a substantially tubular framework delimiting a multiplicity of fenestrations;

a filter device attached to said tubular framework, said filter device comprising:
  frame elements;
  bioabsorbable filter elements attached to said frame elements, and
  suspension elements connected to said filter elements, wherein said filter elements are configured to position said suspension elements towards a center of a lumen, wherein upon bioabsorbtion of said filter elements, said suspension elements re-position against a wall of said lumen, wherein said framework is continuous, non-filamentous, non-braided, and non-interlaced;

wherein said framework is made of a non-blended hydrolysable co-polymeric material comprising an amorphous component with a glass transition temperature that is below ambient body temperature and a crystallizable component that possesses a crystalline melting point in excess of ambient body temperature; and wherein said framework expands radially from a compressed first diameter to an uncompressed second diameter below normal human body temperature without requisite for an externally applied force and without requisite for a thermal transition of said polymeric material.

* * * * *

UNITED STATES PATENT AND TRADEMARK OFFICE
CERTIFICATE OF CORRECTION

PATENT NO. : 9,005,269 B2
APPLICATION NO. : 12/181197
DATED : April 14, 2015
INVENTOR(S) : Joseph R. Armstrong et al.

It is certified that error appears in the above-identified patent and that said Letters Patent is hereby corrected as shown below:

Specification

At column 5, line 56, change "usually transported to an implantation site though a healthy" to "usually transported to an implantation site through a healthy".

At column 15, line 62, change "properties could programmed to bioabsorb next." to "properties could be programmed to bioabsorb next.".

At column 21, line 50, change "throughout the in life period of study." to "throughout the life period of study.".

At column 22, line 36, change "from which the device are such that a thermal transition of the" to "from which the device was made are such that a thermal transition of the".

At column 24, line 12, change "substantially it fenestrations." to "substantially covering it fenestrations.".

Signed and Sealed this
Seventeenth Day of November, 2015

Michelle K. Lee
*Director of the United States Patent and Trademark Office*